United States Patent [19]
Tedder et al.

[11] Patent Number: 5,484,892
[45] Date of Patent: Jan. 16, 1996

[54] MONOCLONAL ANTIBODIES THAT BLOCK LIGAND BINDING TO THE CD22 RECEPTOR IN MATURE B CELLS

[75] Inventors: Thomas F. Tedder, S. Natick; Pablo Engel, Boston, both of Mass.

[73] Assignee: Dana-Farber Cancer Institute, Inc., Boston, Mass.

[21] Appl. No.: 66,309

[22] Filed: May 21, 1993

[51] Int. Cl.$^6$ .................. A61K 39/395; C07K 16/18; C07K 16/28; C12N 5/12
[52] U.S. Cl. .................. 530/388.73; 530/387.3; 530/388.15; 435/70.21; 435/172.2; 435/240.27
[58] Field of Search .............. 435/70.21, 172.2, 435/172.3, 240.27; 424/85.8, 130.1, 133.1, 135.1, 141.1, 143.1, 144.1, 153.1, 154.1; 514/8; 530/350, 387.1, 388.1, 388.15, 387.3, 388.73

[56] References Cited

FOREIGN PATENT DOCUMENTS

WO9118011  11/1991  WIPO.
9118011  11/1991  WIPO .............................. C07K 5/08
9116927  11/1991  WIPO .......................... A61K 39/395

OTHER PUBLICATIONS

Harris et al. Tibtech 11: 42–45 (1993).
Edgington et al. Biotechnology 10: 383–389 (1993).
Clark et al. Ann. Rev. Immunol. 9: 97–127 (1991).
Engel et al. J. Immunol. 150: 4719–4732 (1993).
Aruffo et al., "CD22-*mediated stimulation of T cells regulates T-cell receptor/CD3-induced signaling,*" Immunology 89: 10242–10246 (1992).
Bast et al., "The HB-6, CDw75, and CD76 Differentiation Antigens are Unique Cell–Surface Carbohydrate Determinants Generated by the β–Galactoside α2,6–Sialyltransferase," J. Cell Biol. 116:423 (1992).
Boué et al., "Structural Characterization of the Human B Lymphocyte–Restricted Differentiation Antigen CD22," J. Immunol. 140(1):192–199 (1988).
Cepko et al., "Construction and Applications of a Highly Transmissible Murine Retrovirus Shuttle Vector," Cell. 37:1053–1062 (1984).
Dorken et al., "Expression of cytoplasmic CD22 in B–cell ontogeny. Leukocyte Typing III. White Cell Differentiation Antigens" McMichael, A. J., Oxford University Press. Oxford 474 (1987).
Dorken et al., "HD39 (B3), A B Lineage–Restricted Antigen Whose Cell Surface Expression is Limited to Resting and Activated Human B Lymphocytes," J. Immunol. 136:4470–4479 (1986).
Ling et al., "B–cell and plasma antigens: new and previously defined clusters" In Leukocyte Typing III. White Cell Differentiation Antigens, McMichael, A. J. Oxford University Press. Oxford pp. 302–335 (1987).

(List continued on next page.)

Primary Examiner—Margaret Parr
Assistant Examiner—Phillip Gambel
Attorney, Agent, or Firm—Weingarten, Schurgin, Gagnebin & Hayes

[57] ABSTRACT

The present invention is concerned with a series of novel monoclonal antibodies directed against CD22, a B lineage-restricted member of the Ig-superfamily which serves as an adhesion receptor expressed by mature B lymphocytes and is believed to function in the regulation of B cell activation. The monoclonal antibodies (mAb) specifically block red blood cell and leukocyte adhesion (80–100%) to COS cells transfected with CD22 cDNA and also identify a region of CD22 distinct from those defined by previously described CD22 mAb. The invention also encompasses therapeutic compositions including therapeutically effective amounts of a polypeptide comprising the CD22 ligand or portion thereof or of a polypeptide comprising the first two amino terminal Ig-like domains of CD22, or the ligand binding portion thereof. The antibodies and polypeptides of the invention find use in therapeutic methods for treatment of humans to retard or block CD22 adhesive function, particularly in autoimmune disease.

5 Claims, 11 Drawing Sheets

OTHER PUBLICATIONS

Mason et al., "Value of Monoclonal Anti–CD22 (p135) Antibodies for the Detection of Normal and Neoplastic B Lymphoid Cells," Blood 69:836–840 (1987).

Pezzutto et al., "Amplification of Human B Cell Activation by a Monoclonal Antibody to the B Cell–Specific Antigen CD22, Bp 130/140," J. Immunol. 138: 98–103 (1987).

Pezzutto et al., "Role of the CD22 Human B Cell Antigen in B Cell Triggering by Anti–Immunoglobulin," J. Immunol. 140:1791–1795 (1988).

Powell et al., "Natural Ligands of the B Cell Adhesion Molecule CD22β Carry N–Linked Oligosaccharides with α=2,6–Linked Sialic Acids That Are Required for Recognition," J. Biol. Chem. 268:(10)7019–7027 (1993).

Schwarting et al., "The Monoclonal Antibodies αS–HCL 1 (αLeu–14) and αS–HCL 3 (αLeu–M5) Allow the Diagnosis of Hairy Cell Leukemia," Blood 65(4):974–983 (1985).

Schwartz–Albiez et al., "B5.2 The carbohydrate moiety of the CD22 antigen can be modulated by inhibitors of the glycosylation pathway," B–cell antigens–papers, 65–67.

Sgroi et al., "CD22, a B Cell–specific Immunoglobulin Superfamily Member, Is a Sialic Acid–binding Lectin," J. Biol. Chem. 268(10):7011–7018 (1993).

Shawler et al., "Human Immune Response to Multiple Injections of Murine Monoclonal IgG," Immunol. 135(2):1530–1535 (1985).

Stamenkovic et al., "The B Lymphocyte Adhesion Molecule CD22 Interacts with Leukocyte Common Antigen CD45RO on T Cells and α2–6 Sialyltransferase, CD75, on B Cells," Cell 66:1133–1144 (1991).

Stamenkovic et al., "CD22 Binds to α–2,6–Sialyltransferase–Dependent Epitopes on COS Cells," Cell 68:1003–1004 (1992).

Stamenkovic et al., "The B–cell antigen CD22 mediates monocyte and erythrocyte adhesion," Nature 345:74–77 (1990).

Wilson et al., "cDNA Cloning of the B Cell Membrane Protein CD22: A Mediator of B—B Cell Interactions," J. Exp. Med. 173:137–146 (1991).

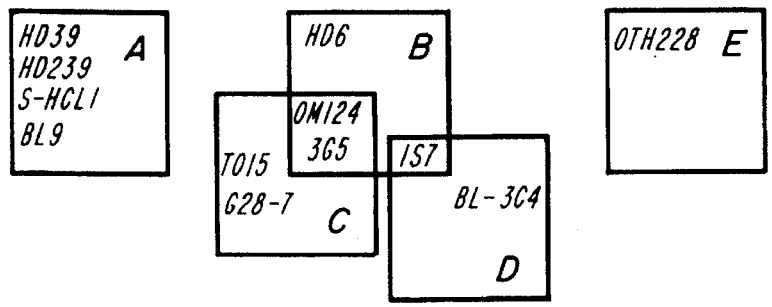
FIG. 3
(PRIOR ART)
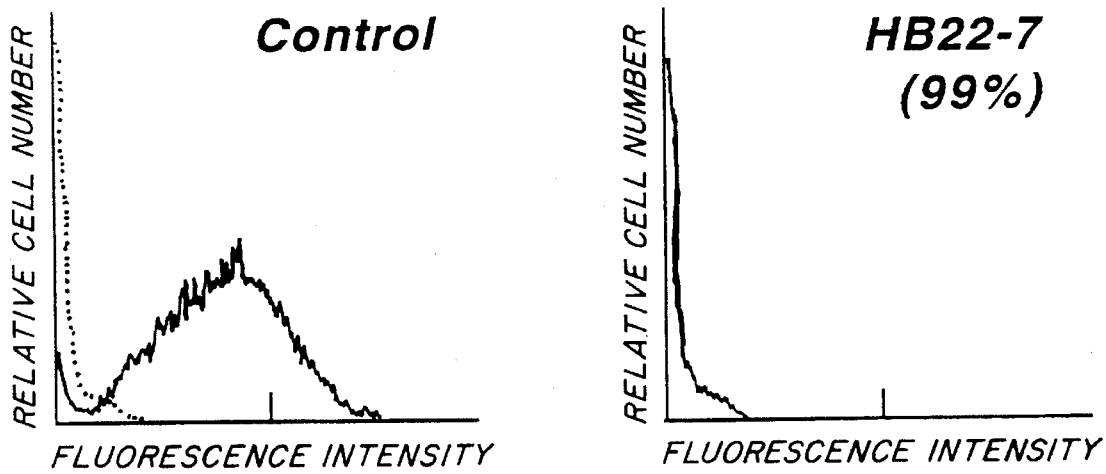
FIG. 4A  FIG. 4B

FIG. 9

| | | I(L)-D(E)-S(T)-P(X)-L | |
|---|---|---|---|
| SEQ ID:NO:1 | HUMAN ICAM-1 D1 | CSTSCDQPKLLG... | IETPL PKK |
| SEQ ID:NO:2 | HUMAN ICAM-2 D1 | CSTTCNQPEVGG... | LETSL NKI |
| SEQ ID:NO:3 | HUMAN ICAM-3 D1 | CSTDCPSSEKIA... | LETSL SKE |
| SEQ ID:NO:4 | HUMAN VCAM-1 D1 | CSTTGCESPFFSWRTQ | IDSPL NGK |
| SEQ ID:NO:5 | HUMAN VCAM-1 D4 | CSVMGCESPSFSWRTQ | IDSPL SGK |
| SEQ ID:NO:6 | HUMAN CD22 D1 | CVWIPCTYRALDGD | LESFI LFH |
| SEQ ID:NO:7 | MOUSE ICAM-1 D1 | CSSSCKEDLSLG... | LETQW LKD |
| SEQ ID:NO:8 | MOUSE ICAM-2 D1 | CSTNCAAPDMGG | LETPT NKI |
| SEQ ID:NO:9 | MOUSE VCAM-1 D1 | CSTTGCESPLFSWRTQ | IDSPL NAK |
| SEQ ID:NO:10 | MOUSE VCAM-1 D4 | CAAIGCDSPSFSWRTQ | TDSPL NGV |
| SEQ ID:NO:11 | MOUSE CD22 D1 | CIRIPCKYKTPLPKAR | LDNIL LFQ |

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 20 amino acids (B) TYPE: amino acid
(D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:1:

Cys Ser Thr Ser Cys Asp Gln Pro Lys Leu Leu Gly Ile Glu Thr Pro
1               5                   10                  15
Leu Pro Lys Lys
            20

(2) INFORMATION FOR SEQ ID NO:2:

(i) SEQUENCE CHARACTERISTICS:
    (A) LENGTH: 20 amino acids
    (B) TYPE: amino acid
    (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:2:

Cys Ser Thr Thr Cys Asn Gln Pro Glu Val Gly Gly Leu Glu Thr Ser
1               5                   10                  15
Leu Asn Lys Ile
            20

(2) INFORMATION FOR SEQ ID NO:3:

(i) SEQUENCE CHARACTERISTICS:
    (A) LENGTH: 20 amino acids
    (B) TYPE: amino acid
    (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:3:

Cys Ser Thr Asp Cys Pro Ser Ser Glu Lys Ile Ala Leu Glu Thr Ser
1               5                   10                  15
Leu Ser Lys Glu
            20

(2) INFORMATION FOR SEQ ID NO:4:

(i) SEQUENCE CHARACTERISTICS:
    (A) LENGTH: 24 amino acids
    (B) TYPE: amino acid
    (D) TOPOLOGY: linear (ii) MOLECULE TYPE: peptide (iii) HYPOTHETICAL: NO ( i v ) ANTI-SENSE: NO ( v ) FRAGMENT TYPE: internal ( x i ) SEQUENCE DESCRIPTION: SEQ ID NO:4:

Cys Ser Thr Thr Gly Cys Glu Ser Pro Phe Phe Ser Trp Arg Thr Gln
1               5                   10                  15

Ile Asp Ser Pro Leu Asn Gly Lys
                20

( 2 ) INFORMATION FOR SEQ ID NO:5:

( i ) SEQUENCE CHARACTERISTICS:
( A ) LENGTH: 24 amino acids
( B ) TYPE: amino acid
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:5:

Cys Ser Val Met Gly Cys Glu Ser Pro Ser Phe Ser Trp Arg Thr Gln
1               5                   10                  15

Ile Asp Ser Pro Leu Ser Gly Lys
                20

( 2 ) INFORMATION FOR SEQ ID NO:6:

( i ) SEQUENCE CHARACTERISTICS:
( A ) LENGTH: 22 amino acids
( B ) TYPE: amino acid
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:6:

Cys Val Trp Ile Pro Cys Thr Tyr Arg Ala Leu Asp Gly Asp Leu Glu
1               5                   10                  15

Ser Phe Ile Leu Phe His
                20

( 2 ) INFORMATION FOR SEQ ID NO:7:

( i ) SEQUENCE CHARACTERISTICS:
( A ) LENGTH: 20 amino acids
( B ) TYPE: amino acid
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:7:

Cys Ser Ser Ser Cys Lys Glu Asp Leu Ser Leu Gly Leu Glu Thr Gln

```
          1               5                    1 0                   1 5

Trp  Leu  Lys  Asp
                   2 0
```

( 2 ) INFORMATION FOR SEQ ID NO:8:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:8:

```
    Cys  Ser  Thr  Asn  Cys  Ala  Ala  Pro  Asp  Met  Gly  Gly  Leu  Glu  Thr  Pro
    1                   5                        1 0                       1 5

Thr  Ser  Asn  Lys  Ile
                   2 0
```

( 2 ) INFORMATION FOR SEQ ID NO:9:

( i ) SEQUENCE CHARACTERISTICS:
        ( A ) LENGTH: 24 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:9:

```
    Cys  Ser  Thr  Thr  Gly  Cys  Glu  Ser  Pro  Leu  Phe  Ser  Trp  Arg  Thr  Gln
    1                   5                        1 0                       1 5

Ile  Asp  Ser  Pro  Leu  Asn  Ala  Lys
                   2 0
```

( 2 ) INFORMATION FOR SEQ ID NO:10:

( i ) SEQUENCE CHARACTERISTICS:
        ( A ) LENGTH: 24 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:10:

```
    Cys  Ala  Ala  Ile  Gly  Cys  Asp  Ser  Pro  Ser  Phe  Ser  Trp  Arg  Thr  Gln
    1                   5                        1 0                       1 5

Thr  Asp  Ser  Pro  Leu  Asn  Gly  Val
                   2 0
```

( 2 ) INFORMATION FOR SEQ ID NO:11:

( i ) SEQUENCE CHARACTERISTICS:
  ( A ) LENGTH: 24 amino acids
  ( B ) TYPE: amino acid
  ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:11:

Cys Ile Arg Ile Pro Cys Lys Tyr Lys Thr Pro Leu Pro Lys Ala Arg
1               5                   10                  15

Leu Asp Asn Ile Leu Leu Phe Gln
            20

( 2 ) INFORMATION FOR SEQ ID NO:12:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:12:

TCAAGTTCTC CCCACAGTGG AGTC  24

( 2 ) INFORMATION FOR SEQ ID NO:13:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:13:

ACCAACTATT ACAACGTGCG CAGG  24

( 2 ) INFORMATION FOR SEQ ID NO:14:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:14:

GAAGTTCCTC TCCAATGACA CG  22

( 2 ) INFORMATION FOR SEQ ID NO:15:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:15:

AAGTGCAGTA TGCCCCGGAA         20

MONOCLONAL ANTIBODIES THAT BLOCK LIGAND BINDING TO THE CD22 RECEPTOR IN MATURE B CELLS

GOVERNMENT RIGHTS

Part of the work leading to this invention was made with United States Government funds. Therefore, the U.S. Government has certain rights in this invention.

FIELD OF THE INVENTION

The invention is directed to antibodies blocking the adhesion of erythrocytes and leukocytes to the CD22 receptor on mature B cells.

BACKGROUND OF THE INVENTION

The proliferation and differentiation of B cells is a complex process directed and regulated through interactions with many other cell types. Among the B cell-specific molecules involved in this process, CD22 is believed to serve a significant role since it is an adhesion molecule of B cells that may function in homotypic or heterotypic interactions (Stamenkovic et al., Nature 344:74 (1990); Wilson et al., J. Exp. Med. 173:137 (1991); Stamenkovic et al., Cell 66:1133 (1991)). The CD22 protein is expressed in the cytoplasm of progenitor B and pre-B cells (Dörken et al., J. Immunol. 136:4470 (1986); Dörken et al., "Expression of cytoplasmic CD22 in B-cell ontogeny. In *Leukocyte Typing III. White Cell Differentiation Antigens*. McMichael et al., eds., Oxford University Press, Oxford, p. 474 (1987); Schwarting et al., Blood 65:974 (1985); Mason et al., Blood 69:836 (1987)), but is found only on the surface of mature B cells, being present at the same time as surface IgD (Dörken et al., J. Immunol. 136:4470 (1986)). CD22 expression increases following activation and disappears with further differentiation (Wilson et al., J. Exp. Med. 173:137 (1991); Dörken et al., J. Immunol. 136:4470 (1986)). In lymphoid tissues, CD22 is expressed by follicular mantle and marginal zone B cells, but only weakly by germinal center B cells (Dörken et al., J. Immunol. 136:4470 (1986); Ling et al., "B-cell and plasma antigens: new and previously defined clusters" In *Leukocyte Typing III. White Cell Differentiation Antigens*, McMichael et al., eds., Oxford University Press, Oxford, p. 302 (1987)). However, in situ hybridization reveals the strongest expression of CD22 mRNA within the germinal center and weaker expression within the mantle zone (Wilson et al., J. Exp. Med. 173:137 (1991)). CD22 is probably involved in the regulation of B cell activation since the binding of CD22 mAb to B cells in vitro has been found to augment both the increase in intracellular free calcium and the proliferation induced after crosslinking of surface Ig (Pezzutto et al., J. Immunol. 138:98 (1987); Pezzutto et al., J. Immunol. 140:1791 (1988)). Other studies have determined, however, that the augmentation of anti-Ig induced proliferation is modest (Dörken et al., J. Immunol. 136:4470 (1986)). CD22 is constitutively phosphorylated, but the level of phosphorylation is augmented after treatment of cells with PMA (Boue et al., J. Immunol. 140:192 (1988)). Furthermore, a soluble form of CD22 inhibits the CD3-mediated activation of human T cells, suggesting CD22 may be important in T cell-B cell interactions (Stamenkovic et al., Cell 66:1133 (1991)).

cDNA that encode the CD22 protein have been isolated by two different research groups, revealing the protein to be a member of the Ig-superfamily homologous with myelin-associated glycoprotein (MAG), carcinoembryonic antigen (CEA), and neural-cell adhesion molecule (N-CAM) (Stamenkovic et al., Nature 344:74 (1990); Wilson et al., J. Exp. Med. 173:137 (1991)). The first CD22 cDNA isolated encodes a protein with 5 extracellular Ig-like domains that mediates monocyte and erythrocyte attachment to COS cells transfected with the cDNA (Stamenkovic et al., Nature 344:74 (1990)). A second isolated CD22 cDNA encodes an extracellular region of 7 Ig-like domains and a cytoplasmic tail having a different COOH sequence that is 23 amino acids longer than the COOH sequence of the first cDNA isolate (Wilson et al., J. Exp. Med. 173:137 (1991)). This full-length CD22 cDNA encodes a protein with a single $NH_2$-terminal V-like domain and 6 C-type domains, which mediates the binding of T and B lymphocytes to transfected COS cells (Stamenkovic et al., Nature 344:74 (1990); Wilson et al., J. Exp. Med. 173:137 (1991)). In vitro translation of a full-length CD22 cDNA generates a 95,000 $M_r$ protein, and the predicted extracellular portion of the molecule has 12 N-linked glycosylation sites (Wilson et al., J. Exp. Med. 173:137 (1991)), which is consistent for a protein of ~140,000 $M_r$. It has been reported that the 7 Ig-like domain species of CD22 is a B cell-specific ligand for CD45RO on T lymphocytes and a receptor for α2,6-sialyltransferase, CDw75, on B lymphocytes (Stamenkovic et al., Cell 66:1133 (1991)).

Competitive binding inhibition studies using $^{125}$I-labelled prototype mAb in a cellular radioimmunoassay (CRIA) on cell line JOK1 have revealed five different epitopes recognized by 12 tested anti-CD22 monoclonal antibodies. Two independent epitopes are represented by mAb HD39, HD239, S-HCL1, and BL9 (epitope A) and OTH228 (epitope E). Three other epitopes represented by mAb HD6 (epitope B), mAb To15, G28-7 (epitope C), and mAb BL-3C4 (epitope D) seemed to be closely related to each other because some mAb showed overlapping reactions. Antibodies OM-124 and 3G5 reacted both with epitopes B and C whereas mAb IS7 reacted likewise with epitopes B and D (Schwartz-Albiez et al., "The carbohydrate moiety of the CD22 antigen can be modulated by inhibitors of the glycosylation pathway." In *Leukocyte Typing IV. White Cell Differentiation Antigens*. Knapp et al., eds., Oxford University Press, Oxford, p. 65 (1989)).

COS cells transfected with a CD22 cDNA lacking Ig-like domains 3 and 4 have been reported as expressing CD22 epitopes A and D and as lacking epitopes B, C and E (Stamenkovic et al., Nature 344:74 (1990)). In rosetting assays using this cDNA to transfect COS cells, mAb that bind to epitope A (S-HCL1) blocked RBC binding while mAb binding to epitope D (BL-3C4) did not block. In contrast, preincubation of transfected COS cells with either anti-epitope A (S-HCL1) or anti-epitope D (BL-3C4) mAb failed to block monocyte cell adhesion, but when both antibodies were used in conjunction, partial blocking was observed. These results suggested that different epitopes of CD22 participate in erythrocyte and monocyte adhesion and that different ligands may be recognized by each epitope (Stamenkovic et al., Nature 344:74 (1990)).

Additional mAb exhibiting an ability to completely block CD22 binding to all leukocyte types would clearly be advantageous. Such mAb could be used in therapeutic methods for treating patients to retard or block B cell function, particularly in autoimmune disease.

SUMMARY OF THE INVENTION

The present invention provides such monoclonal antibodies, HB22, which identify a region of the CD22 receptor that is distinct from those defined by previously described CD22 monoclonal antibodies (mAb). The HB22 mAb of the invention are ubiquitous, having been found in the classes IgA, IgG (specifically sub-classes 2a and 2b), and IgM. The HB22 mAb specifically block adhesion (80–100%) of a wide variety of cell types, including red blood cells, T lymphocytes, B lymphocytes, monocytes and neutrophils, to CD22. Thus, the antibodies of the invention can be useful in therapeutic methods for treatment of patients to retard or block B cell activation, particularly in autoimmune disease.

Most autoimmune diseases result from, or are aggravated by, the production of antibodies reactive with normal body tissues. All antibodies are produced by B cells following antigen stimulation and activation. Therefore, blocking CD22 function, which may be critical for normal B cell adhesive activities, may inhibit the production of antibodies including autoreactive antibodies. This would alleviate the disease mechanism or clinical features associated with many autoimmune syndromes, e.g., immune complex disorders such as those that result in glomerulonephritis, Goodspature's syndrome, necrotizing vasculitis, lymphadenitis, periarteritis nodosa, systemic lupus erythematosis and arthritis. Similarly, other diseases associated with antibody production would include, but not be limited to, thrombocytopenic purpura, agranulocytosis, autoimmune hemolytic anemias, immune reactions against foreign antigens such as fetal A-B-O blood groups during pregnancy, myasthenia gravis, insulin-resistant diabetes, Graves' disease, and allergic responses. In addition, CD22 adhesive activity may be involved in the dissemination and metastasis of human B cell tumors, thereby affecting the growth and aggressiveness of the malignancy.

In therapeutic applications, the HB22 monoclonal antibodies identified to date and similar antibodies (or active portions and chimeric combinations thereof) can react with the CD22 receptor and fully block cell adhesion, retarding or preventing B cell activation or CD22 function in general. Thus, the antibodies of the invention can be used to prepare a composition for treating, e.g., autoimmune disease. The composition comprises a therapeutically effective amount of the antibody in association with a pharmaceutically acceptable carrier vehicle.

The invention also includes methods for identifying the ligand for CD22 on leukocytes and erythrocytes and for using the purified or cloned CD22 ligand or portions thereof as a therapeutic agent. The term "ligand," in general, is meant to include both an entire leukocyte cell or a specific leukocyte cell surface determinant or fragment thereof.

Additionally, the first two amino-terminal Ig-like domains of the CD22 protein itself, particularly the first Ig-like domain, have been determined to encompass the CD22 ligand binding site. Therefore, the first two amino-terminal Ig-like domains, or peptides constituting the ligand binding portions thereof, can be used as therapeutic agents to block or arrest autoimmune disease.

BRIEF DESCRIPTION OF THE DRAWINGS

Other features and advantages of the invention will be apparent from the following description of the preferred embodiments thereof and from the claims, taken in conjunction with the accompanying drawings in which:

FIG. 3 shows the epitope specificity of CD22 mAb of the prior art;

FIG. 9 shows the conserved amino acid motif proposed to be involved in integrin binding to members of the immunoglobulin superfamily.

DESCRIPTION OF THE PREFERRED EMBODIMENTS

Figure 1:
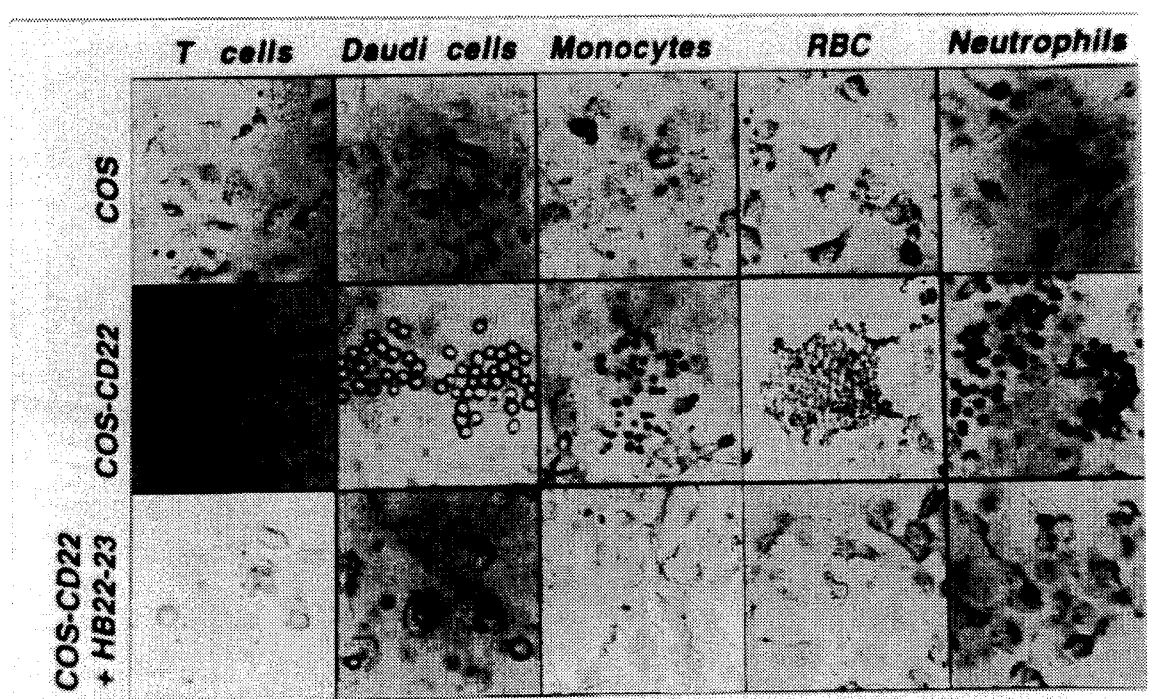
FIG. 1 shows binding of various cell types and cell lines to untransfected COS cells, to COS cells transfected with CD22 cDNA, and to transfected cells in the presence of a monoclonal antibody of the invention.
Figure 2A:
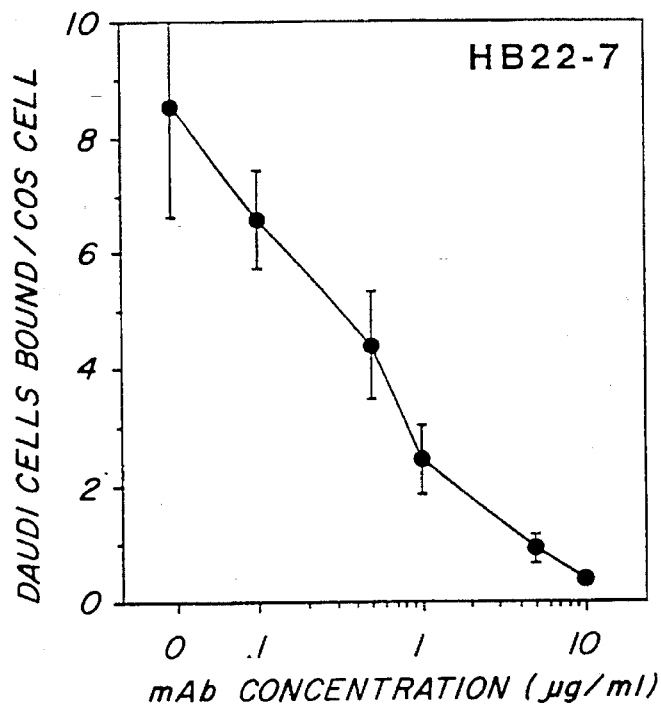
FIG. 2 shows dose response curves for three mAb of the invention compared to a previously described CD22 mAb, HD239.
Figure 2B:
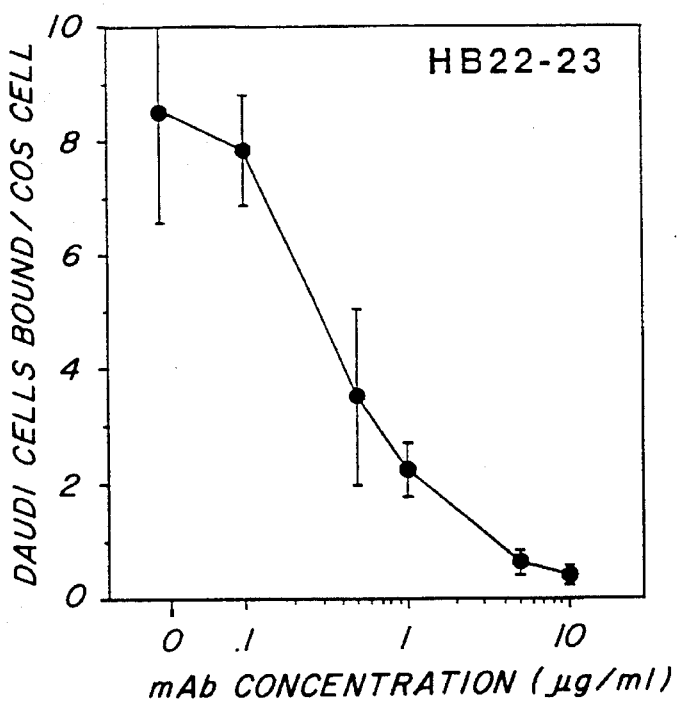
Figure 2C:
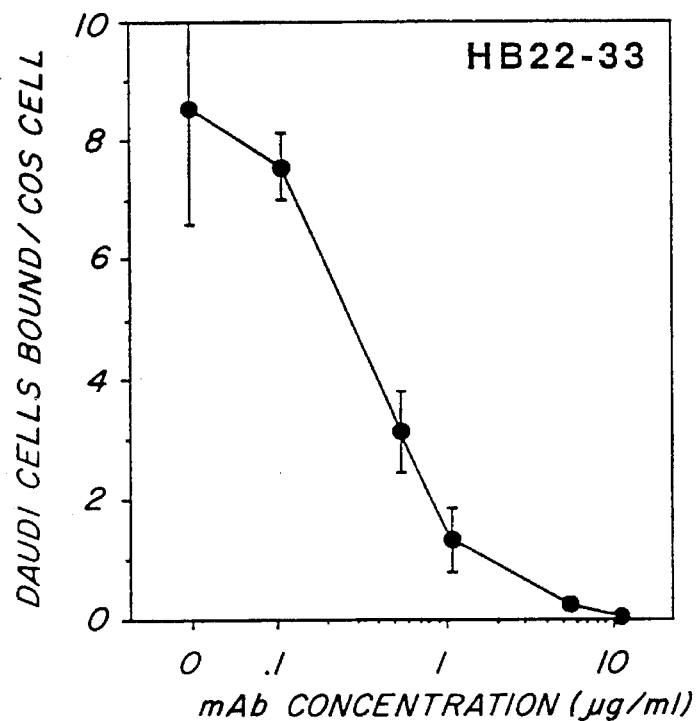
Figure 2D:
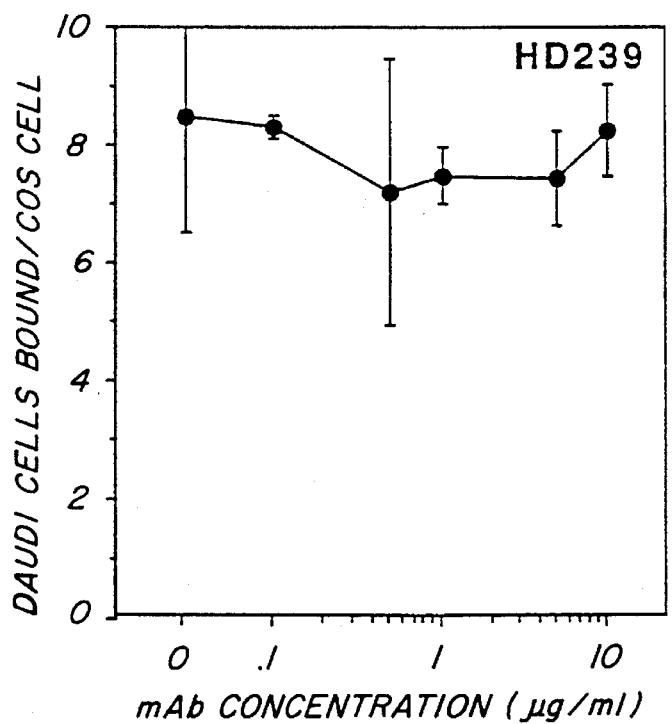
Figure 4C:
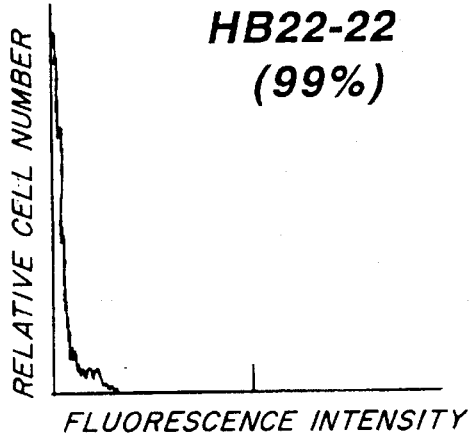
FIG. 4 shows blocking of HB22-7 mAb binding to Daudi cells by CD22 mAb of the invention as compared to previously isolated CD22 mAb.
Figure 4D:
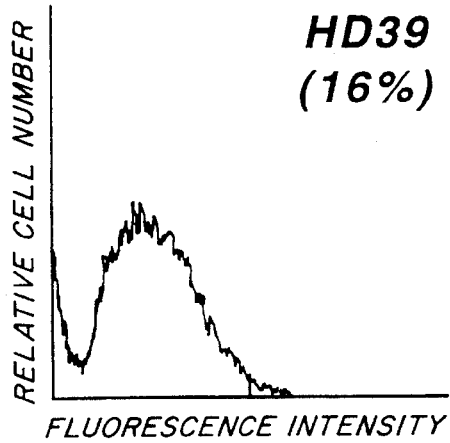
Figure 4E:
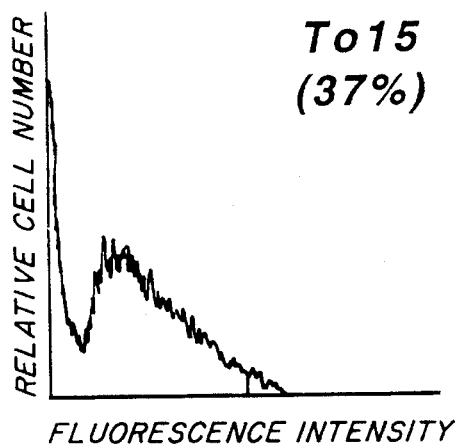
Figure 4F:
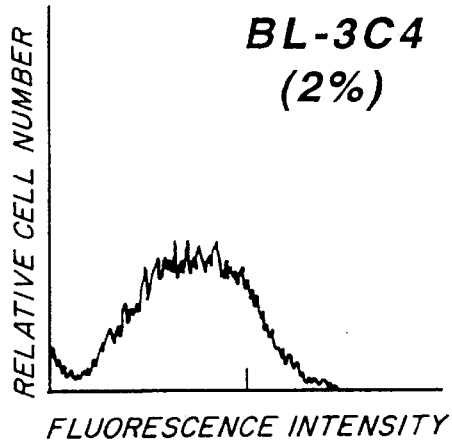

The present invention concerns a series of novel monoclonal antibodies (mAb), designated HB22, that specifically block cell adhesion to CD22, an adhesion receptor expressed by mature B lymphocytes, and therapeutic methods employing the mAb. The HD22 mAb of the invention can be used to retard or block CD22 adhesive function, particularly in autoimmune disease, as described above.

The monoclonal antibody of the invention can be prepared by hybridoma fusion techniques or by techniques that utilize Epstein Barr Virus (EBV)-immortalization technologies (to produce human mAbs), such as are well known by those of skill in the art.

These techniques involve the injection of an immunogen (e.g., purified antigen or cells or cellular extracts carrying the antigen) into an animal (e.g., a mouse) so as to elicit a desired immune response (i.e., production of antibodies) in that animal. In the illustrative example herein, a mouse pre-B cell line, stably transfected with a full-length CD22 cDNA, was used as the immunogen. The cells are injected, for example, into a mouse and, after a sufficient time, the mouse is sacrificed and somatic antibody-producing cells may be derived from the lymph nodes, spleens and peripheral blood of primed animals. Spleen cells are preferred. Mouse lymphocytes give a higher percentage of stable fusions with the mouse myelomas described below. The use of rat, rabbit, frog, sheep and other mammalian somatic cells is also possible. The spleen cell chromosomes encoding desired immunoglobulins are immortalized by fusing the spleen cells with myeloma cells, generally in the presence of a fusing agent such as polyethylene glycol (PEG). Any of a number of myeloma cell lines may be used as a fusion partner according to standard techniques; for example, the P3-NS1/1-Ag4-1, P3-x63-Ag8.653 or Sp2/O-Ag14 myeloma lines. These myeloma lines are available from the American Type Culture Collection (ATCC), Rockville, Md.

The resulting cells, which include the desired hybridomas, are then grown in a selective medium, such as HAT medium, in which unfused parental myeloma or lymphocyte cells eventually die. Only the hybridoma cells survive and can be grown under limiting dilution conditions to obtain isolated clones. The supernatants of the hybridomas are screened for the presence of antibody of the desired specificity, e.g., by immunoassay techniques using the antigen that has been used for immunization. Positive clones can then be subcloned under limiting dilution conditions and the monoclonal antibody produced can be isolated. Various conventional methods exist for isolation and purification of the monoclonal antibodies so as to free them from other proteins and other contaminants. Commonly used methods for purifying monoclonal antibodies include ammonium sulfate precipitation, ion exchange chromatography, and affinity chromatography (see, e.g., Harlow et al., Antibodies. *A Laboratory Manual*, Cold Spring Harbor Laboratory, pp. 1–726, 1988). Hybridomas produced according to these methods can be propagated in vitro or in vivo (in ascites fluid) using techniques known in the art (see, generally, Fink et al., supra. at page 123, FIG. 6-1).

Generally, the individual cell line may be propagated in vitro, for example in laboratory culture vessels, and the culture medium containing high concentrations of a single specific monoclonal antibody can be harvested by decantation, filtration or centrifugation. Alternatively, the yield of monoclonal antibody can be enhanced by injecting a sample of the hybridoma into a histocompatible animal of the type used to provide the somatic and myeloma cells for the original fusion. Tumors secreting the specific monoclonal antibody produced by the fused cell hybrid develop in the injected animal. The body fluids of the animal, such as ascites fluid or serum, provide monoclonal antibodies in high concentrations. As discussed by Cole et al., supra, when human hybridomas or EBV-hybridomas are used, it is necessary to avoid rejection of the xenograft injected into animals such as mice. Immunodeficient or nude mice may be used or the hybridoma may be passaged first into irradiated nude mice as a solid subcutaneous tumor, cultured in vitro and then injected intraperitoneally into pristine primed, irradiated nude mice which develop ascites tumors secreting large amounts of specific human monoclonal antibodies (see Cole et al., supra).

For certain therapeutic applications chimeric (mouse-human) or human monoclonal antibodies may be preferable to murine antibodies, because patients treated with mouse antibodies generate human antimouse antibodies, (Shawler et al., *J. Immunol.* 135:1530–35 (1985)). Chimeric mouse-human monoclonal antibodies reactive with the CD22 antigen can be produced, for example, by techniques recently developed for the production of chimeric antibodies (Oi et al., *Biotechnologies* 4(3):214–221 (1986); Liu et al., *Proc. Nat'l. Acad. Sci.* (USA) 84:3439–43 (1987)). Accordingly, genes coding for the constant regions of the murine HB22 antibody molecules of the invention are substituted with human genes coding for the constant regions of an antibody with appropriate biological activity (such as the ability to activate human complement and mediate antibody dependent cellular cytotoxicity (ADCC)).

According to a preferred embodiment, the antibodies of this invention, designated HB22 mAb, were produced via hybridoma techniques using a mouse pre-B cell line 300.19, stably transfected with full-length CD22 cDNA, as the immunogen as described in the detail below. Individual HB22 hybridomas producing HB22 antibodies of the invention, are identified as HB22-7, HB22-22, HB22-23, and HB22-33. The HB22 mAb produced by the hybridomas listed above are of the IgG2*b*, IgGA, IgG2*a*, and IgM isotype, respectively. The antibodies display a very strong inhibition of binding of a wide variety of cell types to cell surface receptor CD22, a property that has not been shown in previously isolated anti-CD22 mAb (Stamenkovic et al., Cell 66:1133 (1991)).

It should be understood that the present invention encompasses the HB22 antibody described above and any fragments thereof containing the active binding region of the antibody, such as Fab, $F(ab')_2$ and Fv fragments. Such fragments can be produced from the HB22 antibody using techniques well established in the art (see, e.g., Rousseaux et al., in *Methods Enzymol.*, 121:663–69 Academic Press, (1986)).

In addition, the present invention encompasses antibodies that are capable of binding to the same antigenic determinants as the HB22 antibody already identified and competing with these HB22 antibodies for binding at those sites. These include antibodies having the same antigenic specificity as the HB22 antibody of the invention, but differing in species origin or isotype. For example, class, isotype and other variants of the antibody of the invention may be constructed using recombinant class-switching and fusion techniques known in the art (see, e.g., Thammana et al., *Eur. J. Immunol.* 13:614 (1983); Spira et al., *J. Immunol. Meth.* 74:307–15 (1984); Neuberger et al., *Nature*, 312:604–08 (1984); and Oi et al., supra)). Thus, chimeric antibodies or other recombinant antibodies (e.g., antibody fused to a second protein such as a lymphokine) having the same ligand blocking specificity as the HB22 antibody fall within the scope of this invention. Furthermore, the antibody of the invention include all antibodies that specifically block (at the 80% level and above) the adhesion of leukocytes to the CD22 receptor on mature B cells.

The HB22 mAb can be used to isolate and characterize the CD22 ligand and to identify functional ligand-binding regions on CD22. As will be described in more detail below, CD22 has been used as a probe to further identify and characterize the epitope(s) recognized by the antibodies.

Chimeric or other recombinant HB22 antibodies or polypeptides of the invention, as described earlier, may be used therapeutically. For example, a fusion protein comprising at least the antigen-binding region of an HB22 antibody may be joined to a portion of a second carrier protein. Similarly, polypeptides of the invention may also be joined to carrier proteins. In addition, a chimeric HB22 antibody may be formed wherein the antigen-binding region of the mAb may be joined to portions or fragments of a human Ig molecule. Furthermore, recombinant techniques known in the art can be used to construct bispecific antibodies wherein one of the binding specificities of the antibody is that of HB22 (see, e.g., U.S. Pat. No. 4,474,893).

It is apparent therefore that the present invention encompasses pharmaceutical compositions, combinations and methods for blocking CD22 adhesive function. For example, the invention includes pharmaceutical compositions for use in the treatment of autoimmune disease comprising a pharmaceutically effective amount of an HB22 antibody and a pharmaceutically acceptable carrier. The compositions may contain the HB22 antibody, either unmodified, conjugated to a second protein or protein portion or in a recombinant form (e.g., chimeric or bispecific HB22). The compositions may additionally include other antibodies or conjugates.

The antibody compositions of the invention can be administered using conventional modes of administration including, but not limited to, intravenous, intra-arterial, intraperitoneal, oral, intralymphatic or intramuscular. Intravenous administration is preferred. The compositions of the invention can be in a variety of dosage forms, with the preferred form depending upon the mode of administration and the therapeutic application. Optimal dosage and modes of administration for an individual patient can readily be determined by conventional protocols. An effective serum dosage of the antibody compositions of this invention may be in the range of from about 1 to about 100 μg/ml, and preferably 10 μg/ml, resulting in about 1 mg/kg patient body weight.

Isolation of CD22 monoclonal antibody of the invention

The preferred monoclonal antibody of the invention were isolated in a study performed to determine the distribution and biochemical nature of the CD22 ligand(s). The distribution of the ligand(s) for CD22 was analyzed using a panel of different cell types and cell lines that were examined for their ability to bind to COS cells transiently transfected with a full length CD22 cDNA (COS-CD22). Adhesion assays were carried out 48 h after cDNA transfection, and the transfected COS cells were examined for the presence of cellular rosettes. Many of the leukocytes and cell lines examined bound to both untransfected and transfected COS cells when the assays were carried out at room temperature or at 37° C. However, CD22-specific rosette formation with COS-CD22 cells was similar at both 4° and 37° C., so the adhesion assays were carried out at 4° C. to eliminate integrin (CD11/CD18)-mediated and nonspecific cell binding. As shown in Table I, blood T cells and spleen B cells bound avidly to the COS-CD22 cells while they did not attach to COS cells transfected with vector alone. In addition, COS cells transfected with the full-length CD22 cDNA were able to mediate monocyte and erythrocyte attachment as was previously shown for a truncated CD22 cDNA (Stamenkovic et al., Nature 344:74 (1990)). Although not previously reported, as shown in FIG. 1, neutrophils also express CD22 ligand(s) as neutrophil binding to CD22 cDNA transfected COS cells was extensive. All of the pre-B and B cell lines examined bound to the COS cells transfected with CD22 (NALM-6, Daudi, Raji, Ramos, BJAB, Arent and CESS); two of four T cell lines bound (CEM and Jurkat); the K562 erythroleukemia cell line bound; and the HL-60 myelomonocytic cell line did not bind. Interestingly, the mouse pre-B cell line, 300.19, also specifically bound to the human CD22 cDNA-transfected cells, suggesting that the human and mouse CD22 ligands are structurally similar. The specificity of binding for the different cells and cells lines was demonstrated by blocking binding with a newly produced CD22 mAb. Referring to FIG. 1, it can be seen that in the presence of the CD22 mAb HB22 -23 (at 5 μg/ml), binding of blood T cells, Daudi B cells, monocytes, red blood cells (RBC), and neutrophils to transfected COS cells was greatly reduced.

TABLE I

Adhesion of blood cells and cell lines to COS-CD22 cells

| | Cell attachment to:[a] | | Cell expression of:[b] | | |
|---|---|---|---|---|---|
| | COS | COS-CD22 | CD45RO | CDw75 | CD22 |
| Blood Leukocytes: | | | | | |
| T cells | − | +++ | +++ | − | − |
| B cells (spleen) | − | +++ | − | +++ | +++ |
| Monocytes | − | ++ | +++ | + | − |
| Neutrophils | − | +++ | +++ | + | − |
| RBC | − | ++++ | − | ++ | − |
| Cell Lines: | | | | | |
| NALM-6 | − | +++ | − | − | − |
| Raji | − | +++ | + | +++ | ++ |
| Ramos | − | +++ | − | +++ | +++ |
| BJAB | − | ++++ | − | +++ | +++ |
| Arent | + | +++ | + | +++ | ++ |
| Daudi | − | ++++ | − | +++ | +++ |
| CESS | + | +++ | − | +++ | ++ |
| HPB-ALL | − | − | − | − | − |
| CEM | + | +++ | ++ | − | − |
| Jurkat | − | +++ | − | − | − |
| HSB2 | − | − | − | − | − |
| HL-60 | − | − | − | − | − |
| K562 | − | +++ | + | − | − |
| 300.19 (mouse) | − | ++++ | − | − | − |

[a]Cell attachment was assessed by counting the number of test cells bound per rosette positive COS cell. Values represent the relative level of cell attachment to COS cells: −, <1 test cell attached per rosette-forming COS cell; +, mean values of 1–6 cells attached; ++, 6–10 cells attached; +++, 10–20 cells attached; ++++, >20 cells attached. Adhesion was completely inhibited by treatment of the COS cells with the blocking HB22–23 mAb.
[b]CD45RO and CDw75 expression were assessed using the UCHL-1 and OKB-4 mAb, respectively. CD22 was assessed using the HD239 (epitope A) and G28-7 (epitope B and C) mAb, with identical results being obtained for both mAb. Cells were stained by indirect immunofluorescence with flow cytometry analysis; results represent: −, staining identical to background; +, distinct but weak staining; ++, moderate staining intensity; +++, bright staining as described in previous publications (Kansas et al., Eur. J. Immunol. 22:147 (1992)).

Although, CD45RO, CDw75 and CD22 itself have been postulated to represent CD22 ligands, as shown in Table I, cellular adhesion did not strictly correlate with expression of these molecules. For example, the NALM-6 pre-B cell line and the Jurkat T cell line, which do not express these molecules, bound specifically to the transfected COS cells. These results suggest that ligands in addition to CD45RO, CDw75 and CD22 participate in CD22 -mediated adhesion.

A panel of 33 new CD22 mAb were produced to further examine CD22-mediated adhesion, as is described in more detail below. Each mAb was selected as reacting with CD22 cDNA-transfected L cells (fibroblast cell line) and transfected mouse 300.19 cells, but not with untransfected parental cells. In addition, the mAb reacted with the DAUDI and BJAB cell lines, but not with the Jurkat cell line. Furthermore, the mAb reacted with only a small portion of blood lymphocytes (5–10%) consistent with their recognition of CD22 on B cells. As shown in Table II, four of the 33 mAb, HB22-7, HB22-22, HB22 -23 and HB22-33, completely blocked (80–100%) the binding of Daudi, Raji and Jurkat cells to COS-CD22 cells. Four other mAb, HB22-5, HB22-13, HB22-24 and HB22-28, partially blocked adhesion (20–80%) and 25 mAb had little or no effect on cell binding to COS-CD22 cells. mAb HB22-7, HB22-22, HB22-23 and HB22-33 were selected as representing monoclonal antibody of the invention.

TABLE II

Characterization of CD22 mAb

| | | Inhibition of Cell binding to COS-CD22 cells | | | |
|---|---|---|---|---|---|
| | Isotype | Daudi | Raji | Jurkat | RBC |
| New mAb:[a] | | | | | |
| HB22-2 | IgG1 | −[c] | − | − | − |
| HB22-5 | IgG2a | + | + | + | ++ |
| HB22-7 | IgG2b | ++ | ++ | ++ | ++ |
| HB22-12 | IgG2a | − | − | − | − |
| HB22-13 | IgG2a | + | + | + | ++ |
| HB22-22 | IgA | ++ | ++ | ++ | ++ |
| HB22-23 | IgG2a | ++ | ++ | ++ | ++ |
| HB22-24 | IgG1 | + | − | nd | ++ |
| HB22-27 | IgG1 | − | − | − | − |
| HB22-28 | IgG2a | + | + | nd | nd |
| HB22-33 | IgM | ++ | ++ | ++ | ++ |
| Workshop mAb:[b] | | | | | |
| HD39 | IgG1 | − | − | − | − |
| S-HCL1 (Leu-14) | IgG2b | − | − | − | − |
| HD6 | IgG1 | − | − | − | − |
| HD239 | Ig2b | − | − | − | − |
| G28-7 | IgG1 | − | − | − | − |
| 3G5 | IgG1 | − | − | − | ++ |
| IS7 | IgG1 | − | − | − | ++ |
| OTH228 | IgG | − | − | − | − |
| BL9 | IgG1 | − | − | − | − |
| BL-3C4 | IgG2a | − | − | − | − |
| To15 | IgG2b | + | + | + | ++ |

[a] The new mAb were used as hybridoma tissue culture supernatant fluid.
[b] The Workshop mAb (see Materials and Methods) were used as purified mAb at 5 µg/ml except for OTH228, BL9 and To15 that were used as ascites fluid diluted 1:400.
[c] Values represent the amount of blocking of adhesion: −, less than 20% blocking; +, 20–80% blocking; ++, 80–100% blocking.

Characterization of adhesion inhibition by the mAb of the invention

The ability of the mAb of the invention to inhibit red blood cell (RBC) binding to COS-CD22 cells was a more sensitive indicator of mAb blocking ability, as mAb that only partially blocked B cell line attachment could completely block RBC attachment. However, the hybridoma supernatant fluid itself contained an inhibitory substance since supernatant fluid added during the attachment assays in the absence of added mAb blocked RBC attachment to COS-CD22 cells. When the COS-CD22 cells were first treated with supernatant fluid, then washed before the assay, only mAb that blocked cell line attachment to COS cells blocked RBC binding. Each mAb was examined at a concentration two- to six-fold higher than that required for optimal immunofluorescence staining so the failure of most mAb to block binding can not be attributed to low concentrations of mAb.

The four mAb capable of completely blocking (80–100%) cell line and RBC attachment to the CD22 transfected COS cells were selected as those that would be most useful in retarding or preventing CD22 function and, thus, as preferred antibodies of the invention. The HB22-7, HB22-23 and HB22-33 mAb were purified and used to determine the quantity of CD22 mAb necessary to block CD22 receptor function. As shown in FIG. 2, these three mAb were similar in their ability to block the binding of Daudi cells to COS-CD22 cells, with HB22-33 inhibiting slightly more in multiple experiments. On average, these three mAb at concentrations of 10 µg/ml inhibited adhesion by 96%, 5 µg/ml by 92%, 1 µg/ml by 76% and 0.5 µg/ml by 56%. In contrast, the purified, previously described CD22 mAb HD239 had no significant effect on the binding of Daudi cells to COS-CD22.

The ability of other previously described CD22 mAb to inhibit adhesion was also examined. As shown in Table II, of the 11 mAb examined, only the To15 mAb partially (~60%) inhibited adhesion of Daudi cells to COS-CD22 cells. Since the To15 mAb was only available as ascites fluid, Daudi cells were incubated with the mAb, washed and the treated cells were examined for their ability to bind COS-CD22 cells. Again, the To15 mAb inhibited cell line adhesion by ~60%. The HD39 and HD239 mAb were able to inhibit RBC binding as ascites fluid, but purified mAb at 5 µg/ml had no significant inhibitory effect. However, the purified 3G5 and 1S7 mAb completely blocked adhesion of RBC suggesting that these mAb may partially interfere with CD22 function.

Since most leukocyte types bind to COS-CD22 cells, the capacity of individual CD22 mAb of the invention to block binding was examined. Referring to Table II, it can be seen that the CD22 mAb HB22-7, HB22-22, HB22-23 and HB22-33 each completely blocked the binding of DAUDI and RAJI cells, the Jurkat T cell line and RBC to COS-CD22 cells. Similarly, as shown in FIG. 1, the HB22-23 mAb completely blocked T cell, B cell line, neutrophil, monocyte and erythrocyte binding to COS-CD22 cells. These results suggest that each of these cell types binds through the identical region of CD22.

Identification of CD22 epitope(s) for binding of the mAb of the invention.

The region(s) on CD22 that mediates ligand binding was characterized by mAb cross-inhibition studies using the CD22-blocking mAb and a panel of mAb (the Workshop mAb) that identify five different epitopes on CD22 (epitopes A, B, C, D, and E) (Schwartz-Albiez et al., "The carbohydrate moiety of the CD22 antigen can be modulated by inhibitors of the glycosylation pathway." The binding specificities of the Workshop mAb are depicted pictorially in FIG. 3. In *Leukocyte Typing IV. White Cell Differentiation Antigens*, Knapp et al., eds., Oxford University Press, Oxford, p. 65 (1989)). Three of the CD22 blocking mAb of the invention, HB22-7, HB22-22, and HB22 -23 bind to very close or the same epitopes on CD22. As shown in Table III and FIG. 4, each of these mAb is able to cross-block the binding of the other two. Referring to FIG. 4, blocking of HB22-7 mAb binding to Daudi cells by CD22 mAb is shown. Daudi cells were treated with the biotin-labeled HB22-7 mAb alone (control) or after the cells had been treated with saturating concentrations of unlabeled HB22-7, HB22-22, HD39, To15 or BL-3C4 mAb. The cells were then treated with avadin-FITC to assess the binding of the labeled HB22-7 mAb. Cell staining was assessed by flow cytometry analysis and staining with avadin-FITC alone is shown as a dotted line in the first panel. Results are shown on a two decade log scale and the ability of the test mAb to inhibit the binding of labeled HB22-7 mAb is given in parentheses as % inhibition. Of the mAb tested, only the HB22-7 mAb itself and HB22-22 were able to block binding of labeled HB22-7 mAb.

These three new CD22 mAb of the invention bind to a region close to the epitope identified by the HB22-33 mAb as they block its binding as well (as shown in Table III), although not at the same high level. These epitopes are distinct from the epitopes defined by previously characterized CD22 mAb (FIG. 3) as few of these mAb inhibited the binding of the HB22 mAb of the invention. However, the region of CD22 that predominantly mediates ligand binding may be located in close proximity to a region overlapping epitopes B, C and D since, as shown in Table III, the only mAb that significantly block the binding of the HB22-7 and HB22-22 mAb were mAb that partially define epitopes B, C and D. In additional experiments, the HB22-22 mAb was able to also block the binding of the G28-7 (56% inhibition) and 1S7 (41%) mAb, but not the HD6 (2%), 3G5 (25%), BL-3C4 (0%), and OTH228 (0%) mAb. Only binding of the HB22-33 mAb was significantly inhibited by the binding of several of the previously characterized CD22 mAb. However, since the HB22-33 mAb is of the IgM isotype, its large size would make it more readily susceptible to blocking by a previously bound mAb. The HB22-33 epitope is likely to be located near the B epitope since the 3G5 (99% inhibition) and 1S7 (99%) mAb blocked HB22-33 binding, while the HD6 (13%), G28-7 (42%), BL-3C4 (0%) and OTH288 (0%) mAb only partially inhibited binding. These results suggest that a single region of CD22, which may contain more than one epitope, mediates ligand binding activity.

TABLE III

Cross-blocking studies with CD22 mAb

| | Epitopes | Ability of Test mAb to Block the Binding of Labeled: | | | |
|---|---|---|---|---|---|
| | | HB22-7 | HB22-22 | HB22-23 | HB22-33 |
| New mAb: | | | | | |
| HB22-7 | — | 99 | 98 | 93 | 69 |
| HB22-22 | — | 99 | 98 | 97 | 84 |
| HB22-23 | — | 99 | 97 | 99 | 72 |
| HB22-33 | — | 8 | 0 | 36 | 99 |
| Workshop mAb: | | | | | |
| HD39 | A | 16 | 0 | 1 | 3 |
| HD239 | A | 19 | 24 | 22 | 35 |
| S-HCL1 | A | 11 | 9 | 11 | 67 |
| BL9 | A | 5 | 0 | 1 | 13 |
| HD6 | B | 1 | 0 | 0 | 86 |
| 3G5 | B/C | 5 | 1 | 3 | 94 |
| IS7 | B/D | 19 | 57 | 4 | 88 |
| TO15 | C | 37 | 0 | 11 | 0 |
| G28-7 | C | 5 | 0 | 12 | 54 |
| BL-3C4 | D | 2 | 0 | 4 | 0 |
| OTH228 | E | 18 | 0 | 2 | 55 |

Values represent the relative ability of the test mAb to block the binding of the indicated labeled mAb to BJAB cells. Numbers indicate the percentage decrease in the number of fluorescence positive cells as shown in FIG. 4. These results are representative of those obtained in three experiments.

Identification of the CD22 ligand(s)

Figure 5A:
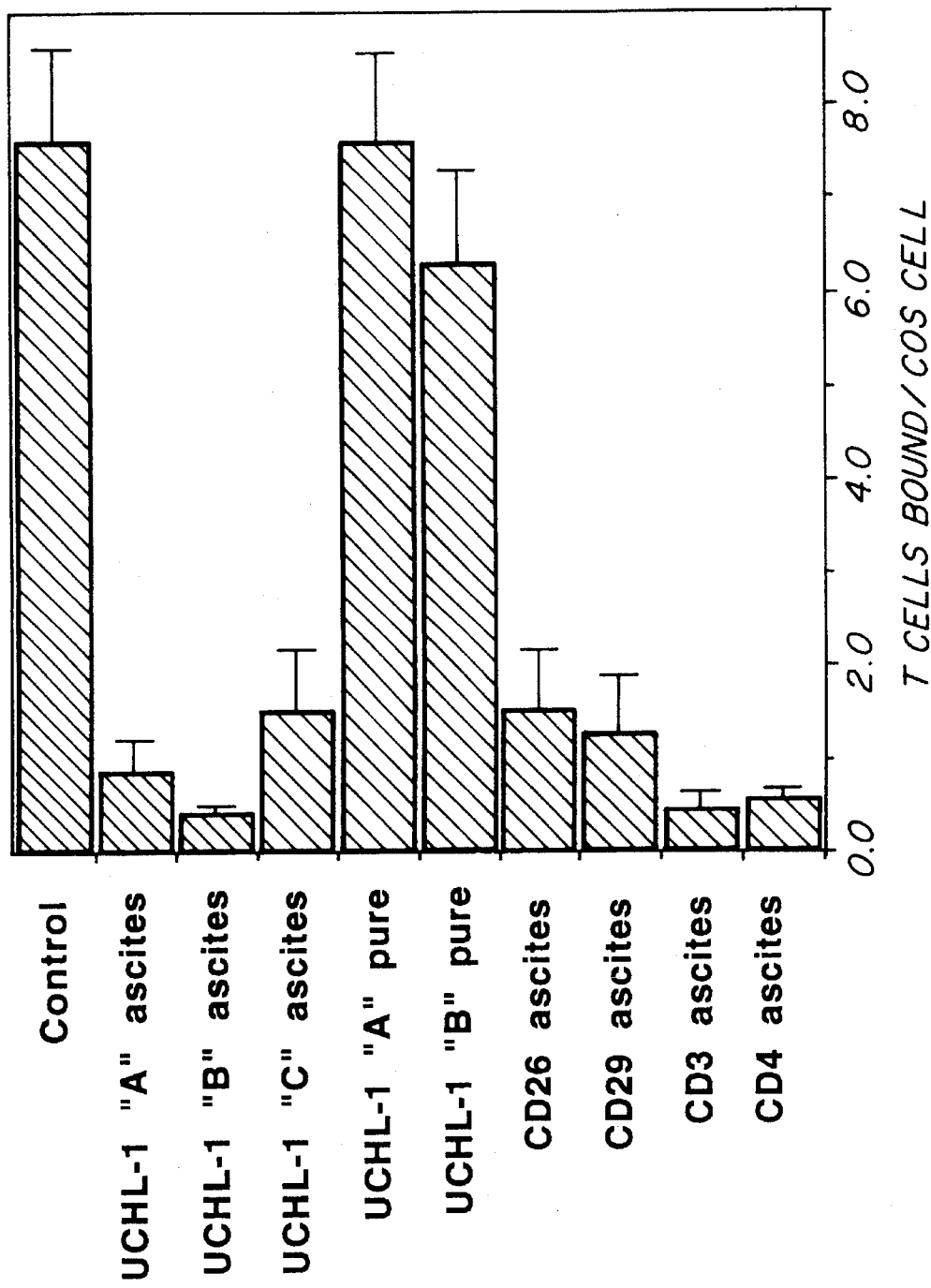
FIGS. 5A and 5B show blockage of T cell and Ramos cell binding, respectively, to CD22 cDNA transfected COS cells by various mAb in ascites fluid form as compared to blockage by the CD45RO mAb UCHL-1 as isolated from ascites fluid.
Figure 5B:
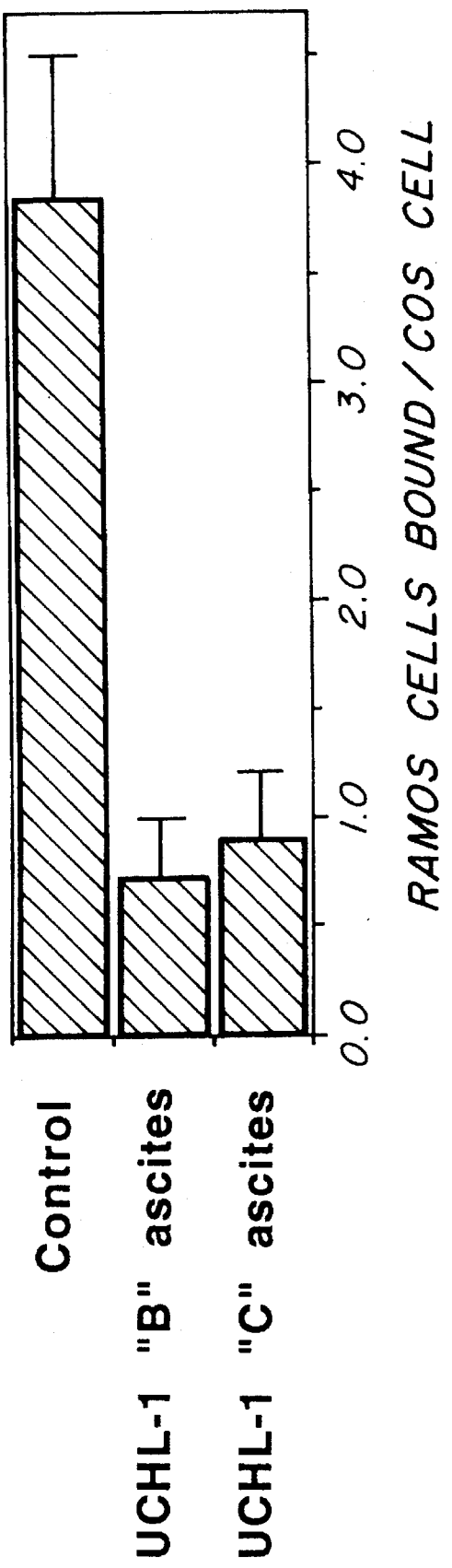

It has been proposed that CD45RO is a ligand for CD22 on T cells and that CDw75 is a CD22 ligand on B cells (Stamenkovic et al., Cell 66:1133 (1991)). This finding was primarily based on the ability of UCHL-1 (CD45RO mAb) and CDw75 mAb to block the binding of lymphocytes to COS-CD22 cells. In an effort to confirm these findings, COS cells were transfected with a full length CD22 cDNA and examined for the ability of different mAb to block the binding of T lymphocytes to transfected cells. As reported, CD45RO mAb in the form of ascites fluid was able to completely block the binding of blood T cells to COS-CD22 cells. However, as shown in FIG. 5A, purified UCHL-1 isolated from the inhibitory ascites fluid did not inhibit T cell binding. Two separate batches of UCHL-1 were examined before purification from ascites fluid and after purification in ten independent experiments with identical results. In none of the experiments did purified UCHL-1 from 1 to 50 µg/ml have any effect on the binding of the T cells to COS-CD22 cells. That ascites fluid was capable of inhibiting CD22-mediated adhesion was also observed for approximately half of the preparations of ascites fluid examined, including mAb reactive with CD26, CD29, CD3 and CD4. Importantly, several unrelated mAb in ascites form partially or completely blocked the subsequent binding of T cells to COS-CD22 cells when added directly to the assay wells at dilutions between 1:100 to 1:500, including mAb which did not react with the target cells in the assay. For example, the Ramos B cell line does not express CD45RO, yet UCHL-1 ascites fluid inhibited >75% of Ramos cell attachment to COS-CD22 cells (FIG. 5B). UCHL-1 ascites fluid also blocked the binding of other CD45RO negative cells (DAUDI and RBC) to COS-CD22 cells. To further determine whether the inhibitory substances were contained in ascites fluid, cells were treated with UCHL-1 ascites fluid or other inhibitory batches of ascites fluid and washed before being added to COS-CD22 cells. In most instances, this treatment completely eliminated the inhibitory activity of the ascites fluid suggesting the presence of a soluble factor in ascites fluid that blocks CD22 binding to its ligand. The soluble factor in ascites fluid may very well be a soluble form of the CD22 cell surface ligand.

The loss of blocking activity for purified UCHL-1 cannot be attributed to a loss of the affinity of the mAb for CD45RO during the purification process since purified mAb preparations generated identical immunofluorescence staining patterns when compared to the ascites fluid from which they were derived. The blood mononuclear cell staining capacity of the "batch A" UCHL-1 shown in FIG. 4 was assessed: ascites fluid (diluted 1:400; ~10 µg/ml, 43% of the cells positive) and mAb purified from ascites fluid (10 µg/ml, 41% of the cells positive). All comparable dilutions of UCHL-1 ascites fluid and purified mAb gave identical results when assessed for indirect immunofluorescence staining with flow cytometry analysis. Purified UCHL-1 mAb at 0.4 µg/ml still stained 44% of cells. Identical results were obtained for "batch B" UCHL-1 ascites fluid and purified mAb. Furthermore, purified UCHL-1 mAb effectively allowed complete removal of CD45RO+ T cells from T cell populations using goat anti-mouse Ig-coated immunomagnetic beads, indicating that the purified mAb preparations had not lost their affinity for antigen. These results strongly suggest that some ascites fluid preparations contain inhibitory substance(s) for CD22 function and that the UCHL-1 mAb does not inhibit the interaction between T cells and COS-CD22 in a specific way. Furthermore, fetal calf serum contained inhibitory substances that blocked RBC adhesion to COS-CD22 cells. FCS at 5% did not block RBC adhesion, but at 10% blocked ~20% of RBC attachment, at 20% blocked 70–80% of RBC attachment and at 40% blocked 100% of RBC adhesion to COS-CD22 cells.

CDw75 has also been proposed to be a ligand for CD22 (Stamenkovic et al., Cell 66:1133 (1991)). Although purified CDw75 mAb were not available to examine this issue directly, it is possible that the previously observed effects of these mAb on CD22-mediated adhesion resulted from ascites fluid effects as well. Therefore, CDw75+ Daudi cells were treated with dilutions of ascites fluid containing saturating concentrations of CDw75 mAb (HH1, HH2, and OKB-4), a CD76 (CRIS-4) mAb or another mAb (HB-6) that identifies carbohydrate structures similar to CDw75 (Bast et al., J. Cell Biol. 116:423 (1992)). The mAb-treated cells were then washed twice prior to being added to the adhesion assays with COS-CD22 cells. Treatment of the B cell lines with these mAb had no effect on cell line attachment, while treatment of the COS cells with the CD22-23 mAb with subsequent washing, completely blocked Daudi cell attachment to the COS cells. Therefore, it does not appear that CDw75 is a ligand for CD22.

It has also been reported that transfection of α2,6-sialyl-transferase into COS cells confers a novel adhesive phenotype that allows binding of soluble recombinant CD22 (Stamenkovic et al., Cell 68:1003 (1992)). This was examined by transfecting COS cells with the β-galactoside α2,6-sialyltransferase that generates expression of the CDw75, CD76 and HB-6 carbohydrate determinants on the surface of COS cells (Bast et al., J. Cell Biol. 16:423 (1992)). While transfection of COS cells with this cDNA induced CDw75, CD76 and HB-6 expression as previously shown, it did not result in detectable binding of CD22$^+$ cells including Raji, Daudi, and BJAB cells. Thus, COS cell over-expression of α2,6-linked sialic acid moieties, including CDw75, is not sufficient to mediate the adhesion of CD22$^+$ B cell lines, suggesting that the binding of the recombinant CD22 protein as previously reported may only be a low avidity interaction.

Figure 6:
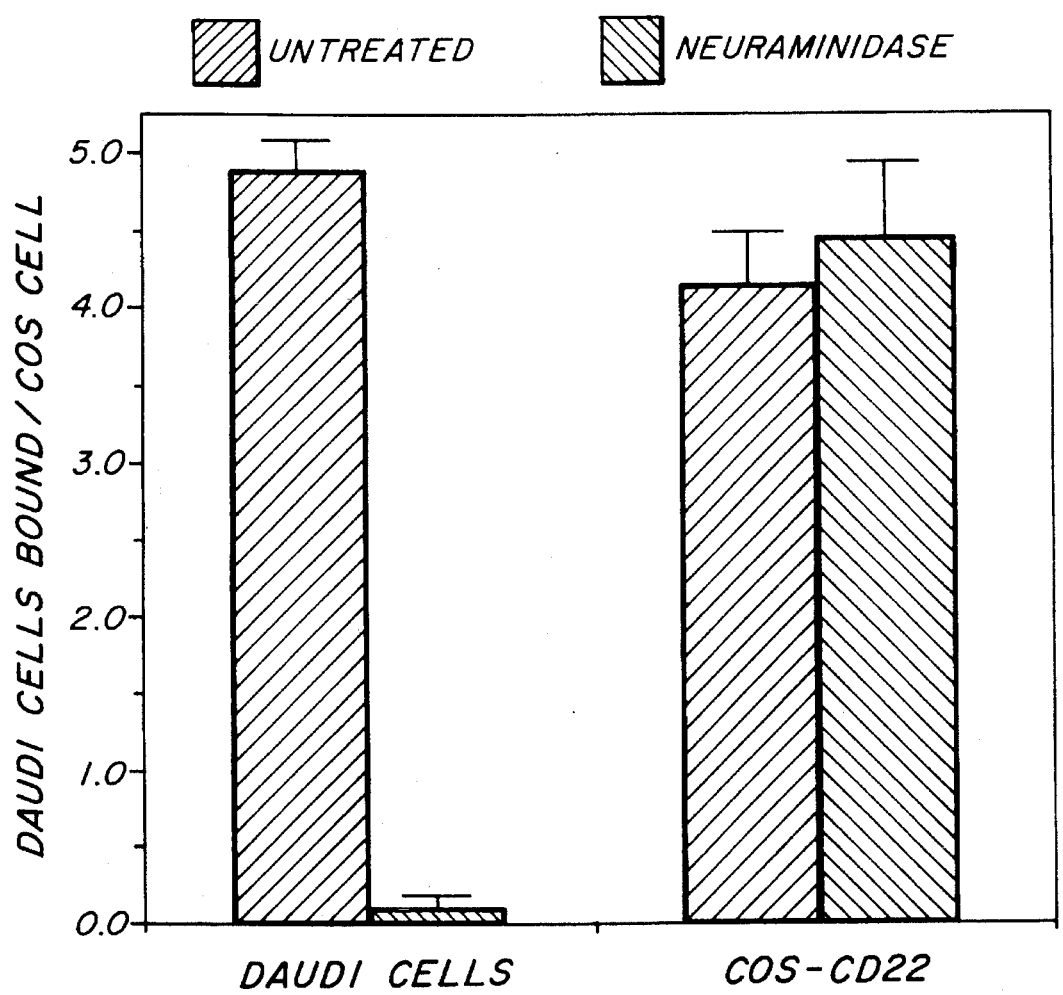
FIG. 6 shows the sensitivity of the CD22 ligand to neuraminidase treatment.

Since the receptor previously reported as a CD22 ligand on B cells, CDw75 (Stamenkovic et al., Cell 66:1133 (1991)), is a sialylated cell surface determinant (Bast et al., J. Cell Biol. 116:423 (1992)), the effect of neuraminidase on CD22 function was examined. As shown in FIG. 6, treatment of Daudi cells with neuraminidase (0.1 U/ml) completely inhibited (98±2%) binding of these cells to COS-CD22 cells. In contrast, treatment of the COS-CD22 cells with neuraminidase had no effect on the binding of Daudi cells. The binding of blood T cells, Jurkat, Raji and Ramos cells and RBC to COS-CD22 cells was also eliminated by treatment of the cells with neuraminidase (>90% inhibition), showing that the CD22 ligand on multiple cell lineages is sialylated. Thus, while sialylation of the CD22 ligand was essential for adhesion, sialylation of CD22 on the COS cells was not. In addition, if the Daudi cells were pre-incubated with each of the CD22 mAb of the invention and washed before being added to COS-CD22 cells, the mAb did not block the binding of the Daudi cells to COS-CD22 cells, while similar pretreatment of the COS-CD22 cells with blocking mAb completely inhibited Daudi binding. These findings suggest that CD22 does not act as its own homotypic counter-receptor for B cell adhesion.

Whether the receptor for CD22 was an integrin was examined by carrying out the adhesion assays without divalent cations present. The COS-CD22 cells were gently fixed for ~1 min in 2% (v/v) formaldehyde and washed with Ca$^{++}$/Mg$^{++}$ free PBS containing 10 mM EGTA or EDTA before Daudi cells that had been similarly washed were added. This treatment had no detectable effect on Daudi attachment compared to DMEM-treated cells. In addition, the presence of multiple anti-integrin mAb at saturating levels did not block Daudi attachment, including mAb directed against CD11a, CD18, CD29, CD49d, CD49e, CD49f, and CD31. Therefore, it appears that the CD22 ligand may represent a novel surface structure not previously recognized to be involved in cellular adhesion.

Cell surface expression of CD22

Figure 7A:
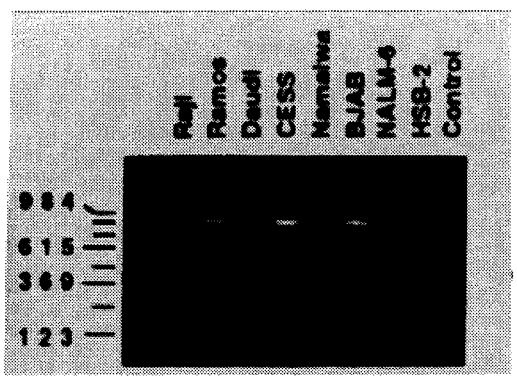
FIGS. 7A–7C show hybridization of CD22 isoforms generated from different B cell lines to probes corresponding to the second and fifth Ig-like domains of CD22, the second domain of CD22, and the junction of domains 3 and 4, respectively.
Figure 7B:
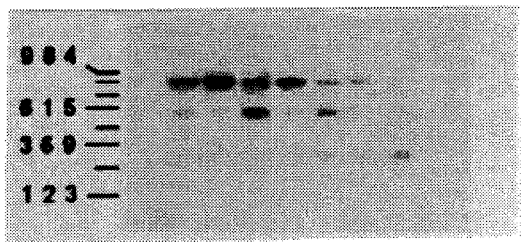
Figure 7C:
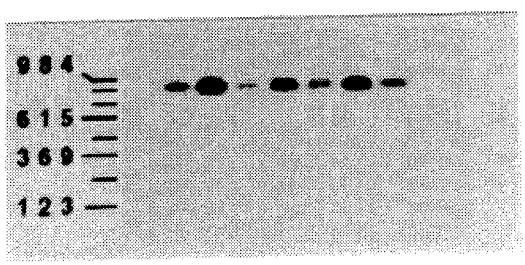

Two isoforms of CD22 cDNA have been isolated, suggesting that B cells may express multiple isoforms of CD22 generated through alternative splicing of a single gene, deleting the third and fourth Ig-like domains. Similarly, Northern blot analysis of mRNA from B cell lines has revealed one major transcript of 3.3 kb and several smaller transcripts (Wilson et al., J. Exp. Med. 173:137 (1991)). In order to examine the role of different CD22 isoforms, CD22 cDNA were generated from different B cell lines, amplified by PCR and analyzed by Southern blot analysis. Referring to FIG. 7A, three specific bands were identified when the cDNA were amplified using oligonucleotides corresponding to sequences within the second and fifth Ig-like domains of CD22 : a predominant band of ~900 bp, and bands of ~600 and ~350 bp. The major band corresponds to the full-length form of CD22 whereas the two smaller bands correspond to forms of CD22 lacking domains 3 and/or 4. This was confirmed by Southern blot analysis, as shown in FIG. 7B, since all three bands hybridized with a probe corresponding to the second domain of CD22 . Only the largest band hybridized with a probe directed against the junctions of domains 3 and 4 (FIG. 7C). Furthermore, nucleotide sequencing of the smaller band revealed splice junctions identical to those already described (Stamenkovic et al., Nature 344:74 (1990)). Restriction endonuclease digestion of 16 independent cDNA subclones containing the intermediate sized PCR product indicated that this band corresponded, in all cases, to a CD22 isoform that lacks the fourth Ig-like domain. PCR amplification of the full-length CD22 cDNA using the same primers generated only the larger band indicating that the primers were not inappropriately binding to other regions of CD22 cDNA and generating spurious DNA bands. The same pattern of bands and hybridization was found with all seven B cell lines analyzed, including the pre-B cell line NALM-6 which expresses CD22 only intracytoplasmically. No bands were observed with the T cell line HSB2. Therefore, it appears that while mRNA isoforms representing splicing variants of CD22 exist, they do not appear to be restricted to specific B cell lines.

Figure 7D:
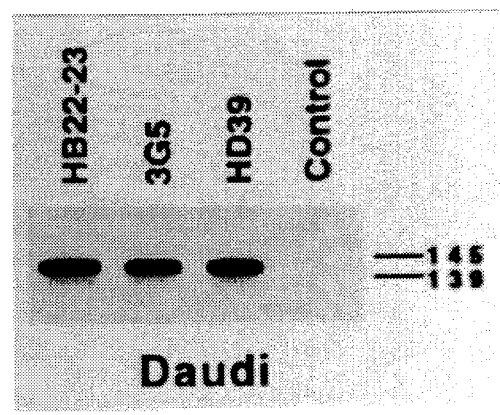
FIGS. 7D and 7E show expression of cell surface CD22 isoforms by Daudi and BJAB cell lines, respectively.
Figure 7E:
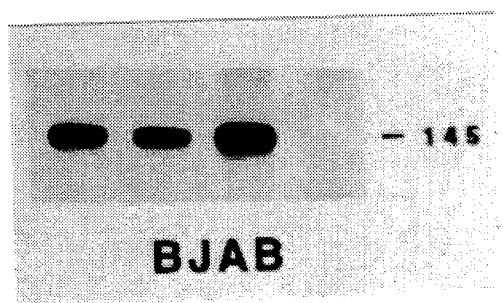

Immunoprecipitation studies were carried out to determine if different isoforms of CD22 were expressed on the cell surface. The HD39 mAb, which recognizes epitope A, the 3G5 mAb which recognizes epitopes B and C, and the HB22-23 mAb which recognizes the ligand-binding region of CD22 were used to immunoprecipitate CD22 from the B cell lines BJAB and Daudi. Referring to FIGS. 7D and 7E, all three mAb generated the same pattern of immunoprecipitated proteins, precipitating only one band of ~145,000 $M_r$ from the B cell line BJAB and two bands of ~145,000 and 139,000 $M_r$ from the B cell line Daudi. As shown in FIG. 7D, the 139,000 $M_r$ band expressed by Daudi cells represented a minor portion of labeled protein and was precipitated by all three mAb with similar efficiencies. Since both CD22 isoforms are seen in reducing and nonreducing conditions and epitopes B and C are reported to be absent in the shorter isoform of CD22 (Stamenkovic et al., Cell 66:1133 (1991)), the smaller 135,000 $M_r$ species of CD22 would not be precipitated by the 3G5 mAb if it were generated by mRNA lacking Ig-like domains 3 and 4. Therefore, it appears that a single protein species of CD22 is expressed on the cell surface and that the mAb which block CD22-mediated function precipitate quantitatively and qualitatively similar proteins as those that do not block CD22 function.

Since Daudi cells expressed two isoforms of CD22 and BJAB cells expressed only a single detectable isoform, both cell types were analyzed by indirect immunofluorescence with all of the CD22 mAb listed in Table II with subsequent flow cytometry analysis. In all cases, each mAb stained the both cell lines at similar levels. Therefore, it is highly unlikely that any of the mAb used in these studies identifies epitopes present on the minor isoform of CD22 that are not found on the dominant isoform.

The region of CD22 that mediates ligand binding is contained within Ig-like domains 1 and 2

The CD22 isoform expression studies reported above suggested that the ligand binding region of CD22 is located on or within the amino-terminal Ig-like domains of the receptor. Furthermore, studies by others (Stamenkovic et al., Cell 66:1133 (1991)) had shown that the three amino terminal Ig-like domains of CD22 were required for mAb binding to epitopes A, B, C, and E and for the binding of a T cell (Molt-4) and a B cell (Daudi) line. Construction and expression of truncated forms of CD22 with only the first Ig-like domain of CD22 did not bind any of the CD22 mAb in their study identifying epitopes A, B, C, D, and E or result in cell binding. Expression of the first two Ig-like domains resulted in one epitope A mAb binding, but no cell binding. Therefore, their studies suggested that the third Ig-like domain was essential for reactivity of most mAb and for cell binding.

Figure 8:
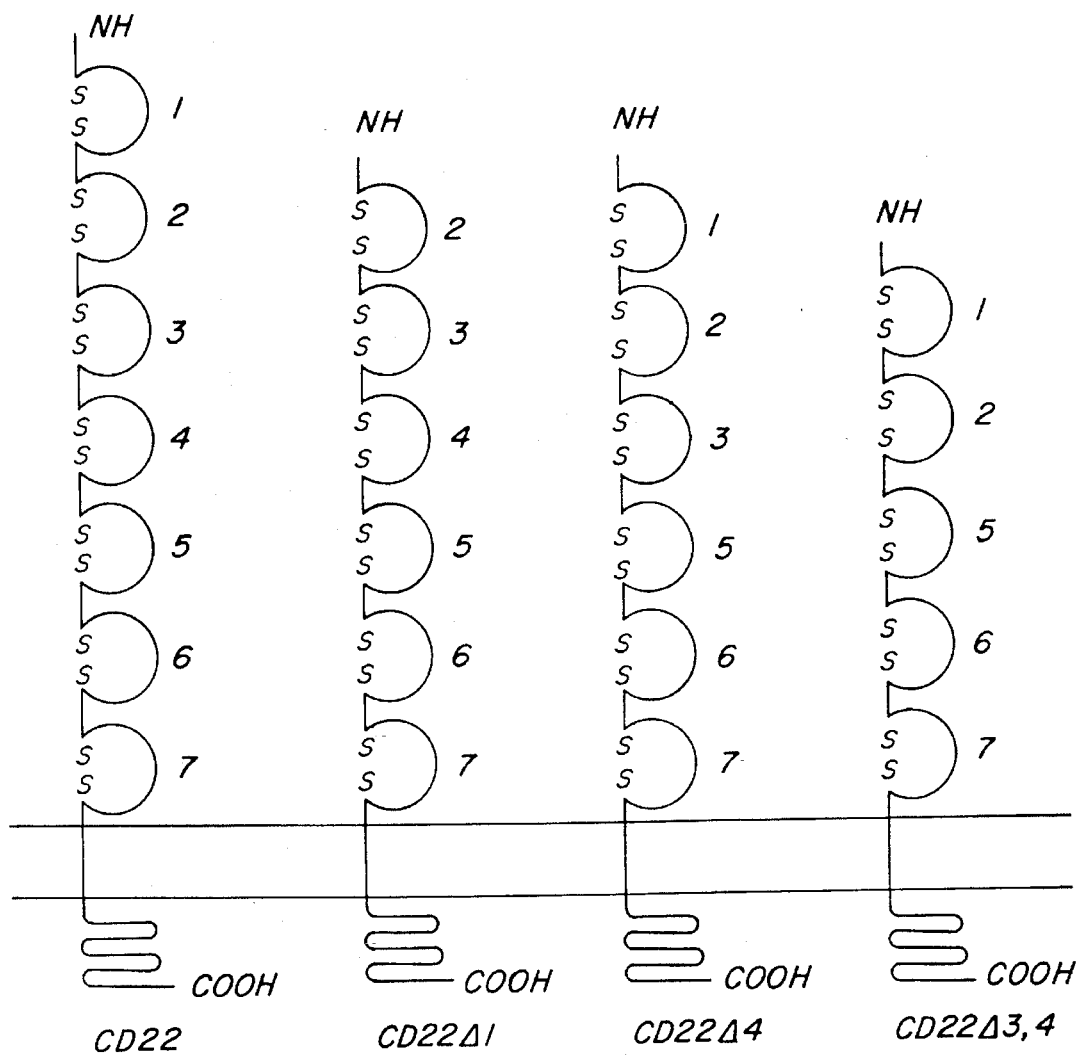
FIG. 8 shows a schematic drawing of truncated forms of CD22.

To examine which domains of CD22 contained the epitopes identified by the HB22 mAb and which domains mediated cell binding, a truncated form of the CD22 molecule lacking the first Ig-like domain was created. This truncated form was produced by introducing a new unique restriction site (EcoR V) at the beginning of the first Ig-like domain of CD22 cDNA using polymerase chain reaction (PCR). Using other convenient restriction sites within the full length CD22 cDNA, three pieces of DNA were ligated together: 1) a Hind III/EcoR V fragment which encodes the leader sequence of CD22; 2) a large Hind III/Kpn I fragment containing the pSP64 vector and the 3' end of CD22; and 3) a Stu I/Kpn I fragment starting at the beginning of the second Ig-like domain and containing the rest of the CD22 cDNA. This new truncated form of CD22 cDNA lacking the first Ig-like domain (CD22 $\Delta$1) was subcloned in the PMT2 expression vector. Similarly, two truncated forms of the CD22 cDNA lacking the 3rd and 4th Ig-like domains (CD 22 $\Delta$3-4) and the 4th domain (CD22 $\Delta$4) were generated using the reverse transcriptase PCR products that correspond to the two splice variants of CD22 as shown in FIG. 7a. Unique Nco I restriction sites present in the CD22 cDNA were used to place the truncated PCR-generated fragments into the full-length cDNA, thereby removing the 3rd and 4th domains, and the 4th domain. These CD22 cDNA were then subcloned into PMT2. Schematic drawings of the truncated forms of CD22 are shown in FIG. 8.

COS cells were transfected with the truncated CD22 cDNA (CD22 $\Delta$1, CD22 $\Delta$3-4 and CD22 $\Delta$4) and with a full-length CD22 cDNA. After 48 hours of culture, the transfected COS cells were fixed and assayed for CD22 mAb binding using the different CD22 mAb and a peroxidase-conjugated anti-mouse Ig antiserum. All mAb bound to CD22 cDNA transfected COS cells (Table IV). However, most of the HB22 mAb did not bind to CD22 $\Delta$1 transfected cells, indicating that these mAb bind to epitopes within the first Ig-like domain or to epitopes dependent on the presence of the first Ig-like domain. The binding of all CD22 mAb previously characterized as binding to epitope A (FIG. 3) was lost with removal of the first Ig-like domain. Furthermore, binding of the HB22-7, HB22-22, HB22-23 and HB22-33 mAb which completely block CD22 receptor function was eliminated by removal of the first Ig-like domain. Moreover, binding of two of the HB22 mAb which partially block CD22-mediated adhesion was also tested demonstrating that these mAb were also dependent on the first Ig-like domain. In contrast, two of the previously described Workshop mAb which partially inhibited CD22 binding to red blood cells bound to the CD22$\Delta$1 and CD22$\Delta$4 cDNA transfected cells, yet did not bind to COS cells expressing CD22 $\Delta$3-4, demonstrating that these mAb bound to domain 3 or domain 3-related epitopes. Furthermore, the To15 mAb, which partially blocked leukocyte adhesion to CD22, bound to CD22$\Delta$1 cDNA transfected cells, yet did not bind to COS cells expressing CD22$\Delta$3-4 or CD22$\Delta$4, suggesting that this mAb bound to domain 4. Therefore, it is likely that all CD22 receptor blocking activity associated with this mAb was likely to have resulted from the presence of the ascites fluid-associated blocking factor rather than the mAb itself having blocking activity. From these studies, it appears that all CD22 mAb which block ligand binding bind to the first Ig-like domain or to epitopes which are associated with the first Ig-like domain. (See summary in Table V.)

TABLE IV

Reactivity of CD22 mAb with Truncated CD22 Proteins

| | COS-CD22 | COS-CD22 $\Delta$1 | COS-CD22 $\Delta$3-4 | COS-CD22 $\Delta$4 | COS |
|---|---|---|---|---|---|
| mAb: | | | | | |
| HB22-2 | +++ | ++ | − | +++ | − |
| HB22-5 | +++ | − | ++ | +++ | − |
| HB22-7 | +++ | − | +++ | +++ | − |
| HB22-12 | ++ | +++ | +++ | +++ | − |
| HB22-13 | +++ | − | +++ | +++ | − |
| HB22-17 | +++ | − | +++ | +++ | − |
| HB22-18 | + | − | + | ++ | − |
| HB22-19 | +++ | − | +++ | +++ | − |
| HB22-22 | +++ | ND | +++ | +++ | − |
| HB22-23 | +++ | − | +++ | +++ | − |
| HB22-25 | + | +++ | − | − | − |
| HB22-33 | ++ | − | ++ | ++ | + cyto |
| Workshop mAb: | | | | | |
| HD39 | +++ | − | +++ | +++ | − |
| S-HCL1 | +++ | − | +++ | +++ | + cyto |
| HD6 | +++ | ++ | − | +++ | − |
| HD239 | +++ | − | +++ | +++ | − |
| G28-7 | +++ | +++ | − | − | − |
| 3G5 | +++ | +++ | − | +++ | + cyto |
| IS7 | +++ | ++ | − | +++ | − |
| To15 | ++ | +++ | − | − | − |
| BL-3C4 | +++ | +++ | +++ | +++ | − |

ND = not determined;
cyto = mAb reactive with cytoplasmic antigens not present on the cell surface. Values representing the levels of mAb binding are described in Table I.

TABLE V

Summary Table of CD22 monoclonal antibodies

| | Epitopes | Blocking CD22-mediated adhesion[a] | Cross-blocking with HB22 epitope | Ig Domain Binding |
|---|---|---|---|---|
| CD22 mAb: | | | | |
| HB22-7 | new | 89 ± 3 | >90% | 1 |
| HB22-22 | new | 88 ± 2 | >90% | 1 |
| HB22-23 | new | 91 ± 3 | >90% | 1 |
| Workshop mAb: | | | | |
| HD39 | A | no | no | 1 |
| HD239 | A | no | no | 1 |
| S-HCL1 | A | no | no | 1 |
| BL9 | A | no | no | ND |
| HD6 | B | no | no | 3 |
| 3G5 | B/C | only RBC | no | 3 |
| IS7 | B/D | only RBC | partially | 3 |
| To15 | C | 40 ± 13 | partially | 4 |
| G28-7 | C | no | no | 4 |
| BL-3C4 | D | no | no | 2[b] |
| OTH228 | E | no | no | ND |

[a]Percent blocking of Daudi cells binding to COS-CD22 cells. Values represent the mean ± SD obtained in side-by-side comparisons. Adhesion assays were carried out exactly as in Table II except the HB22 mAb were used 5 µg/ml.
[b]The epitope identified by this mAb is most likely to be located within domain 2, but may be undomain 5, 6 or 7 based on the current data.

The ability of the CD22 truncation mutants to bind leukocytes was also assessed to determine which domains mediate cell adhesion. COS cells transfected with the full-length CD22, CD22Δ3-4 and CD22Δ4 cDNA supported adhesion to equivalent levels of two B cell lines (Raji and BJAB), one T cell line (REX) and red blood cells. In contrast, COS cells expressing CD22Δ1 did not mediate any detectable cell attachment. These results demonstrate that CD22-mediated adhesion requires the first Ig-like domain, but not the 3rd and 4th Ig-like domains. Furthermore, in combination with the results obtained with the function blocking HB22 mAb these results indicate that the ligand binding region of the CD22 molecule is located in the first domain. However, it is possible that there is a contribution from the second Ig-like domain to cell attachment.

That the ligand-binding region of CD22 is located within the first Ig-like domain of CD22 is supported by independent studies where we have identified residues within a conserved amino acid motif found within cell-binding domains of intercellular adhesion molecule-1 (ICAM-1), ICAM-2, ICAM-3, and vascular cell adhesion molecule (VCAM)-1 (Vonderheide et al., submitted for publication). In these studies, we characterized very late antigen (VLA)-4 binding sites in VCAM-1 based on domain deletion and amino acid substitution mutants, similar to the strategy previously used above for CD22 and previously used to identify receptor binding sites in ICAM-1 for its integrin receptors LFA-1 and Mac-1. In a series of experiments, domain deletion mutants of VCAM and ICAM were analyzed for expression and lymphoid cell binding, and compared to wild-type forms. The domain specificities of anti-VCAM-1 and anti-ICAM-1 mAb were also determined and compared to the ability of the mAb to inhibit cell binding. In a second series of experiments, amino acid substitution mutations were targeted to ligand-binding domains. Our results not only demonstrated an independent VLA-4 binding sites in domain 1 and domain 4 of VCAM-1, but we also demonstrate a critical binding function for residues within a conserved five-amino acid sequence found in domain 1 and domain 4 as well as in several other ICAM domains (FIG. 9 and SEQ ID NOS: 1–11). We propose that integrin binding to these Ig-like domains depends on the expression of this conserved motif, and that additional non-conserved sequences in VCAM-1 and ICAM-1 binding domains confer specificity for integrin binding for the appropriate ligand. In relation to these studies, we have taken the information obtained in that study and applied it to all Ig-like domains in CD22. Only the first Ig-like domain of CD22 contained this conserved motif (FIG. 9 and SEQ ID NOS: 1–11), consistent with all data above that this domain mediates the adhesive properties of CD22. That this motif is present within CD22 and is completely conserved implies that CD22 may be bound by an integrin or a similar adhesion receptor. Nonetheless, these results indicate that specific regions within the first Ig-like domain of CD22 are likely to confer adhesive properties to this molecule.

Isolation of additional CD22 mAb

Additional mAb of the invention can easily be isolated and screened in large numbers. For example, following the isolation method reported herein in Materials and Methods, additional monoclonal antibody, which are potentially mAb of the invention, can be generated. These candidate mAb of the invention can be screened in a functional assay as described herein, which determines the ability of the candidate mAb to block (more than 80%) the adhesion of leukocytes to COS cells transfected with CD22 cDNA. Any other type of standard assay cell line (e.g., CHO or mouse L cells) can be used in such an assay. Alternatively, recombinant CD22 protein may be bound to an insoluble matrix or surface as the testing agent. As the mAb of the invention have been determined to block adhesion of T cells, B cells, monocytes, neutrophils, red blood cells and their respective cell lines or malignancies to the CD22 receptor when the standard of blockage is taken as greater than 80%, any individual leukocyte cell type can be used as the test cell in a screening assay.

The mAb of the invention of any isotype are useful for standardization and comparison purposes. For therapeutic use, preferably mAb of the IgA or IgG isotype are employed. Antibodies of the IgM isotype, although useful for many purposes described herein, are generally not useful as therapeutic agents because of their general low affinity for antigen, difficulty in isolation, ability to activate complement following antigen binding, and difficulty in modification. Therefore, while mAb analogous to HB22-33 are useful as research reagents and will be useful for the characterization of the CD22 ligand, they are generally less useful for therapeutic applications.

MATERIALS AND METHODS

Antibodies. Thirty-three mAb reactive with CD22 were generated by the fusion of NS-1 myeloma cells with spleen cells from Balb/c mice immunized three times with a mouse pre-B cell line, 300.19, stably transfected with a full-length CD22 cDNA. Hybridomas producing mAb reactive with mouse L cells transfected with CD22 cDNA, but not with untransfected cells, were cloned twice and used to generate supernatant or ascites fluid. mAb isotypes were determined using the Mouse Monoclonal Antibody Isotyping Kit (Amersham, Arlington Heights, Ill.). IgGmAb were purified using the Affi-Gel Protein A MAPS II Kit (Bio-Rad, Richmond, Calif.). The HB22-33 mAb (IgM) containing euglobulin fraction of ascites fluid was precipitated by extensive dialysis against distilled water and was shown to be essentially pure mAb by SDS-PAGE analysis. Other CD22 mAb, HD39, HD239, S-HCL1 (Leu-14), BL9, OM124, 3G5, To15, G28-7, IS7, BL-3C4 and OTH228, were obtained from the Fourth International Workshop on Human Leukocyte Differentiation Antigens (Dörken et al., "B-cell antigens: CD22." In *Leukocyte Typing IV. White Cell Differentiation Antigens*, Knapp et al., eds., Oxford University Press, Oxford, p. 63 (1989)). Other mAb used include: the UCHL-1 mAb (CD45RO, hybridoma provided by Dr. Peter C. L. Beverley, Imperial Cancer Research Fund, London, UK) (Smith et al., Immunology. 58:63 (1986)); the 1F7 (CD26), 4B4 (CD29), RW2-4B6 (CD3) and 19Thy-5D7 (CD4) mAb (provided by Dr. Stuart Schlossman, Dana-Farber Cancer Inst., Boston, Mass.); and the 8F2 (VLA α4 chain, CDw49d), 2G6 (VLA α5 chain, CDw49e), 2C3A (VLA α6 chain, CDw49f) and 1F11 (CD31, PECAM-1) mAb provided by Dr. Chikao Morimoto (Dana-Farber Cancer Inst.); and 10F12 (CD18) and 2F12 (CD11a) mAb provided by Dr. Jerry Ritz (Dana-Farber Cancer Inst.). CDw75 mAb were from the Fourth International Leukocyte Differentiation Antigen Workshop (Dörken et al , . "B-cell antigens: CDw75". In "Leukocyte Typing IV. White Cell Differentiation Antigens". Knapp et al., eds. Oxford University Press, Oxford, p. 109 (1989)). Except as indicated, all mAb were used as diluted (1:200 to 1:400) ascites fluid.

Cells. Peripheral blood mononuclear cells were isolated by Ficoll-Hypaque density gradient centrifugation of heparinized blood obtained from healthy donors according to protocols approved by the Human Use Committee of Dana-Farber Cancer Inst. Blood T lymphocytes were isolated from adherent cell-depleted mononuclear cells by rosette formation with sheep erythrocytes (Pellegrino et al., Clin. Immunol. Immunopathol. 3:324 (1975)) and were greater than 98% $CD2^+$ as determined by indirect immunofluorescence staining and flow cytometry analysis. B lymphocytes were isolated from human spleen by depletion of sheep RBC rosetting cells and were >95% $CD20^+$. Monocytes were isolated by incubation of blood mononuclear cells on plastic dishes for 1 h at 37° C. and the adherent cells (~98% $CD15^+$) were harvested by scraping. Blood neutrophils (~98% $CD15^+$) were isolated by centrifugation on Mono-Poly Resolving Medium (Flow Laboratories, McLean, Va.) and RBC were isolated from the red cell pellet after Ficoll-Hypaque sedimentation of blood.

Cell lines were cultured in RPMI 1640 media (Gibco-BRL, Gaithersburg, Md.) supplemented with 10% FCS, L-glutamine, streptomycin and penicillin. Stable cDNA-transfected cells were produced using a full-length CD22 cDNA cloned into the BamH I site of the retroviral vector pZipNeoSV(X) (Cepko et al., Cell 37:1053 (1984)). A mouse pre-B cell line (300.19) and fibroblast (L) cell line were transfected with this vector by electroporation with subsequent selection of stable transfectants using G418 (Gibco-BRL). Antibiotic resistant cells expressing CD22 were identified by indirect immunofluorescence staining and clones expressing high levels of CD22 were selected.

Immunofluorescence analysis. Indirect immunofluorescence analysis was carried out after washing the cells twice. Suspensions of viable cells were analyzed for surface antigen expression by incubation for 20 min on ice with the appropriate mAb as ascites fluid diluted to the optimal concentration for immunostaining. After washing, the cells were treated for 15 min at 4° C. with FITC-conjugated goat anti-mouse Ig antibodies (Southern Biotechnology Associates, Birmingham, Ala.). Single color immuno-fluorescence analysis was performed on an Epics Profile flow cytometer (Coulter Electronics, Hialeah, Fla.). Ten thousand cells were analyzed in each instance and all histograms are shown on a three decade log scale.

Adhesion assays. COS cells were transfected with a full-length CD22 cDNA in the CDM8 expression vector (Wilson et al., J. Exp. Med. 173:137 (1991)) by the DEAE-dextran method. After 24 h, the cells were trypsinized and transferred to 35 mm dishes (Falcon-Becton Dickinson, Lincoln Park, N.Y.) and cultured for an additional 24 h. The cells and cell lines to be used in the adhesion assay were washed and resuspended with DMEM (Gibco-BRL) without serum and incubated with the transfected COS cells ($2 \times 10^6$ cells per 35 mm dish) for 30 min at 4° C. Cells that did not bind to COS cells were removed by extensive washing with DMEM and the cellular rosettes were fixed in DMEM containing 2% (v/v) formalin. The binding of test cells to COS-CD22 cells was quantified in two ways; either by counting the number of test cells bound per field of COS cells thereby indicating the average number of cells bound per COS cell or by determining the mean number of test cells bound per rosette-forming COS cell. In both cases, a minimum of 200 COS cells were counted per assay.

For cellular-adhesion blocking experiments, cDNA-transfected COS cells were pre-incubated with different concentrations of purified CD22 mAb at 4° C. for 30 min before being washed twice with DMEM. The test cells or cell lines were washed twice with DMEM, incubated with the appropriate mAb at 4° C. for 30 min, washed again with DMEM and added to the dishes containing COS cells. In some instances, the test mAb were added to the culture dishes during the adhesion assays as indicated in the figure legends. Neuraminidase treatment was carried out by incubating the COS-CD22 or test cells with 0.1 U/ml of Vibrio collar neuraminidase (Calbiochem, La Jolla, Calif.) at 37° C. for 30 min.

Radiolabeling of cells. BJAB or Daudi cells ($5 \times 10^7$ in 200 μl of PBS) were washed twice with cold PBS and surface labeled with $^{125}I$ using a modified Bolton-Hunter method (Thompson et al., Biochem. 26:743 (1987)). Briefly, Sulfo-SHPP (1 μg per $10^6$ cells) was added to an Iodogen (Pierce, Rockford, Ill.) coated glass tube (100 μg/tube), followed by the addition of 1 mCi of $^{125}I$ (NEN-DuPont, Boston, Mass.). The cells were then added and allowed to incubate for 30 min at room temperature with occasional shaking. Free $^{125}I$ was washed away with cold PBS prior to cell lysis.

Immunoprecipitation analysis. Radiolabelled cells were lysed at 4° C. in 1 ml of lysis buffer containing 1% Triton X-100 (v/v) (Sigma Chemical Co., St. Louis, Mo.), 150 mM NaCl, 10 mM triethanolamine, pH 7.8, 0.5 mM EDTA, 0.1% (w/v) $NAN_3$, 0.2 mg/ml soybean trypsin inhibitor, 0.2 μg/ml leupeptin, 0.2 μg/ml pepstatin, 100 trypsin inhibitory U/ml of aprotinin, 1 mM PMSF, and 20 mM iodoacetamide as described (Tedder et al., Molec. Immunol. 25:1321 (1988)). Detergent insoluble materials and nuclei were removed by centrifugation at 10,000 rpm for 25 min at 4° C. The lysate was then precleared for 3 h with 50 μl of a 50% suspension of Protein G-Sepharose 4B (Pharmacia-LKB Biotechnology, Piscataway, N.J.) and 1 μl of ascites fluid containing an unreactive mAb. The lysates were divided equally and precipitated overnight at 4° C. with 2 μl of three different CD22 mAb or control CD3 mAb as ascites fluid plus 30 μl of Protein A-Sepharose. Immune complexes were washed with alternating high salt RIPA and low salt RIPA buffers two times each and once with PBS. Immunoprecipitated samples were boiled for 5 min in 50 μl of sample buffer (0.1M Tris-HCl, pH 6.8, containing 10 v/v glycerol and 1% SDS), electrophoresed on a 10% SDS-PAGE gel, dried and autoradiographed. $M_r$ were determined using pre-stained standard molecular weight markers (Gibco-BRL).

mAb cross-blocking experiments. BJAB cells (1×10⁶) were first incubated with 10-fold saturating concentrations of test CD22 mAb as diluted ascites fluid (1:100) for 30 min on ice. After incubation, a second biotinylated CD22 mAb was added at an optimal concentration for immunofluorescence staining. After 30 min of further incubation, the cells were washed twice with PBS and incubated for 30 min with fluorochrome-labeled avidin (Sigma). After washing the cells twice, the immunofluorescence staining was assessed immediately by flow cytometry analysis.

In other experiments, BJAB cells were treated with the HB22-22, and HB22-33 mAb at 10 fold saturating concentrations followed by incubation with six of the Workshop mAb at optimal concentrations for immunostaining. The reactivity of the Workshop mAb was assessed by staining the cells with FITC-labeled goat anti-mouse IgG-specific antibodies (Sigma) which did not react with HB22-22, and HB22-33. Immunofluorescence staining was assessed as above.

RNA isolation and cDNA synthesis. RNA was isolated by a modification of the single step acid-guanidinium-phenol-chloroform method from B cell lines as described (Sleasman et al., Eur. J. Immunol. 20:1357 (1990)). cDNA synthesis was performed in a 20 µl volume containing 1 µg of total cellular RNA, 200 U of Superscript RNase H reverse transcriptase (BRL, Gaithersburg, Md.), 1 mM (each) dNTP, 20 U RNasin (Promega, Madison, Wis.), and 100 pmole of random hexamer (Pharmacia-LKB), in 50 mM Tris-HCl (pH 8.3), 75 mM KCl, 10 mM DTT, and 3.0 mM MgCl$_2$. After 60 minutes incubation at 45° C. and denaturation at 95° C., half of the reaction mixture was added to 90 µl of polymerase chain reaction (PCR) dilution buffer (50 mM KCl, 10 mM Tris-HCl, pH 8.3, 1.5 mM MgCl$_2$ and 0.001% gelatin) containing 30 pmol of a sense oligonucleotide primer (5' TCAAG TTCTCCCCACAGTGGAGTC, SEQ ID NO:12) homologous with a nucleotide sequence in the second Ig-like domain, 30 pmol of an antisense oligonucleotide primer (5' ACCAACTATTACAACGTGCGCAGG, SEQ ID NO:13) found in Ig-like domain 5, and Taq polymerase (2.5 U, Perkin-Elmer Corporation, Norwalk, Conn.). The reaction mixture was overlayered with mineral oil and amplification was carried out for 35 cycles on a Perkin-Elmer thermal cycler as follows: 1 min at 94° C., 1 min at 65° C. and 1 min at 72° C.

Synthetic oligonucleotides used for Southern blot analysis were a sense oligonucleotide from within Ig-like domain 2 (5'-GAAGTTCCTCTCCAATGACACG, SEQ ID NO:14) and a sense oligonucleotide at the junctional border of Ig-like domains 3 and 4 (5'- AAGTGCAGTATGCCCCG-GAA, SEQ ID NO:15). Oligonucleotides were 5' end-labeled in a 30 µl reaction containing 20 pmol of oligonucleotide, 30 U T4 polynucleotide kinase (BRL), and 0.15 mCi γ-($^{32}$P)-ATP (NEN-DuPont, Boston, Mass.), in 50 mMTris-HCl (pH 7.6), 10 mM MgCl$_2$, 5 mM DTT, 0.1 mM spermidine-HCl, and 0.1 mM EDTA. After incubation of the mixture for 30 min at 37° C., labeled oligonucleotides were purified by column chromatography. The specific activities of the oligonucleotide probes were ~10⁷ cpm/pmol. The PCR amplified cDNA (10 µl of the reaction mixture) were electrophoresed through 1% agarose gels in 1X TBE with 0.5 µg/ml ethidium bromide, and photographed on a UV transilluminator before transfer to nitrocellulose. Hybridization of the 5' end-labeled oligonucleotides was performed at 50° C. in buffer containing, 6 X SSC, 10 X Denhardts solution, 0.1% SDS (w/v), 20 mM sodium phosphate, and 100 µg/ml salmon sperm DNA (Sigma). Filters were finally washed in 1 X SSC at room temperature. Autoradiography was at room temperature for 30 min.

Deposits

The following hybridoma were deposited on May 14, 1993, with the American Type Culture Collection (ATCC), 12301 Parklawn Drive, Rockville, Md. 20852.

| Hybridoma | ATCC Accession No. |
|---|---|
| HB22-7 | HB11347 |
| HB22-22 | HB11348 |
| HB22-23 | HB11349 |

Applicants' assignee, Dana-Farber Cancer Institute, Inc., represents that the ATCC is a depository affording permanence of the deposit and ready accessibility thereto by the public if a patent is granted. All restrictions on the availability to the public of the material so deposited will be irrevocably removed upon the granting of a patent. The material will be available during the pendency of the patent application to one determined by the Commissioner to be entitled thereto under 37 CFR 1.14 and 35 USC 122. The deposited material will be maintained with all the care necessary to keep it viable and uncontaminated for a period of at least five years after the most recent request for the furnishing of a sample of the deposited microorganism, and in any case, for a period of at least thirty (30) years after the date of deposit or for the enforceable life of the patent, whichever period is longer. Applicants' assignee acknowledges its duty to replace the deposit should the depository be unable to furnish a sample when requested due to the condition of the deposit.

While the present invention has been described in conjunction with a preferred embodiment, one of ordinary skill, after reading the foregoing specification, will be able to effect various changes, substitutions of equivalents, and other alterations to the compositions and methods set forth herein. It is therefore intended that the protection granted by Letters Patent hereon be limited only by the definitions contained in the appended claims and equivalents thereof.

What is claimed is:

1. A monoclonal antibody produced by a hybridoma cell line selected from the group consisting of HB22-7 (ATCC No. HB 11347), HB22-22 (ATCC No. HB 11348) and HB22-23 (ATCC No. HB11349); or a monoclonal antibody that binds to the same antigenic determinant as a monoclonal antibody produced by a hybridoma cell line selected from the group consisting of HB22-7 (ATCC No. HB 11347), HB22-22 (ATCC No. HB 11348) and HB22-23 (ATCC No. HB11349); or an Fab, F(ab')$_2$, or Fv fragment or conjugate of a monoclonal antibody produced by a hybridoma cell line selected from the group consisting of HB22-7 (ATCC No. HB 11347), HB22-22 (ATCC No. HB 11348) and HB22-23 (ATCC No. HB 11349).

2. The monoclonal antibody of claim 1 which is a human antibody.

3. The monoclonal antibody of claim 1 which is a chimeric mouse-human antibody.

4. A hybridoma cell line selected from the group consisting of HB22-7 (ATCC No. HB 11347), HB22-22 (ATCC No. HB 11348) and HB22-23 (ATCC No. HB 11349).

5. A continuous cell line that produces a monoclonal antibody, wherein said monoclonal antibody binds to the same antigenic determinant as a monoclonal antibody produced by a hybridoma cell line selected from the group consisting of HB22-7 (ATCC No. HB 11347), HB22-22 (ATCC No. HB 11348) and HB22-23 (ATCC No. HB 11349).

\* \* \* \* \*

UNITED STATES PATENT AND TRADEMARK OFFICE
CERTIFICATE OF CORRECTION

PATENT NO. : 5,484,892
DATED : January 16, 1996
INVENTOR(S) : Thomas F. Tedder

It is certified that error appears in the above-indentified patent and that said Letters Patent is hereby corrected as shown below:

Column 17 in Table V, line 30 "undomain" should read --in domain--.

Column 18, line 47, "HB22-33" should read --HB-33--.

Signed and Sealed this

Fourth Day of June, 1996

Attest:

BRUCE LEHMAN

*Attesting Officer*   *Commissioner of Patents and Trademarks*